(12) United States Patent
Yanagisawa

(10) Patent No.: US 6,894,514 B2
(45) Date of Patent: May 17, 2005

(54) CIRCUIT PATTERN DETECTING APPARATUS AND CIRCUIT PATTERN INSPECTING METHOD

(75) Inventor: Takayuki Yanagisawa, Tokyo (JP)

(73) Assignee: Toppan Printing Co., Ltd., Tokyo (JP)

( * ) Notice: Subject to any disclaimer, the term of this patent is extended or adjusted under 35 U.S.C. 154(b) by 0 days.

(21) Appl. No.: 10/295,847

(22) Filed: Nov. 18, 2002

(65) Prior Publication Data

US 2003/0094938 A1 May 22, 2003

Related U.S. Application Data

(63) Continuation of application No. PCT/JP01/10478, filed on Nov. 30, 2001.

(30) Foreign Application Priority Data

Dec. 1, 2000  (JP) ...................................... 2000-366788
Oct. 11, 2001  (JP) ...................................... 2001-313771

(51) Int. Cl.[7] ...................... G01R 31/302; G01R 31/00
(52) U.S. Cl. ........................................ 324/750; 324/96
(58) Field of Search .................. 324/96, 750, 754–755, 324/501; 439/482; 250/306–307, 310–311

(56) References Cited

U.S. PATENT DOCUMENTS

| | | | |
|---|---|---|---|
| 4,806,776 A | * | 2/1989 | Kley ..................... 250/559.24 |
| 4,906,922 A | | 3/1990 | Takahashsi et al. |
| 5,459,394 A | * | 10/1995 | De Kort et al. ............. 324/750 |
| 5,808,473 A | * | 9/1998 | Shinagawa et al. ......... 324/750 |
| 5,999,005 A | * | 12/1999 | Fujii et al. ................... 324/750 |

FOREIGN PATENT DOCUMENTS

| | | |
|---|---|---|
| JP | 5-256794 | 10/1993 |
| JP | 6-3375 A | 1/1994 |
| JP | 6-175092 A | 6/1994 |
| JP | 7-92236 | 4/1995 |
| JP | 7-134147 A | 5/1995 |
| JP | 7-18121292 A | 7/1995 |
| JP | 9-72947 | 3/1997 |
| JP | 2000-292755 A | 10/2000 |

OTHER PUBLICATIONS

International Search Report, PCT/JP01/10478 (PCT/ISA/210) mailed Feb. 26, 2002.

* cited by examiner

*Primary Examiner*—David Zarneke
*Assistant Examiner*—Jermele Hollington

(57) ABSTRACT

A transparent conductive layer is formed under a glass substrate. A reflection preventing layer and a reflecting layer are formed on the respective surfaces of an electro-optic crystal layer. The reflection preventing layer of the electro-optic liquid crystal layer is attached to the lower surface of the transparent conductive layer by use of an adhesive layer. In this manner, the reflection preventing layer is provided between the adhesive layer and the electro-optic crystal layer.

11 Claims, 13 Drawing Sheets

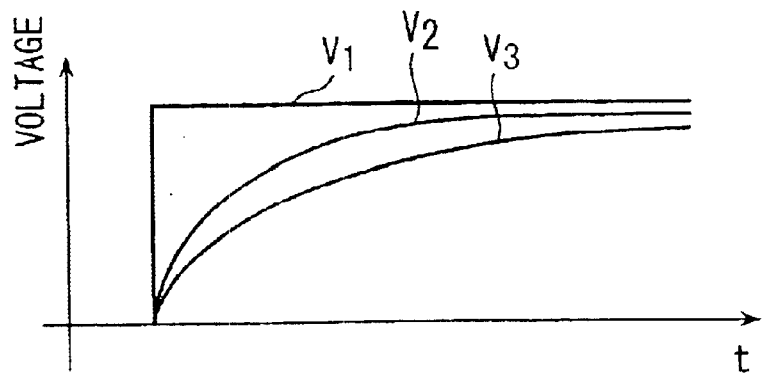
FIG. 7
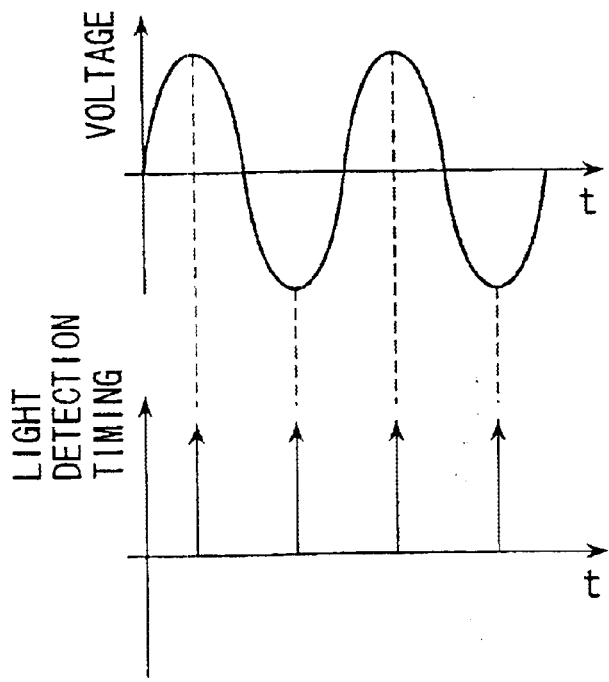
FIG. 8A
FIG. 8B
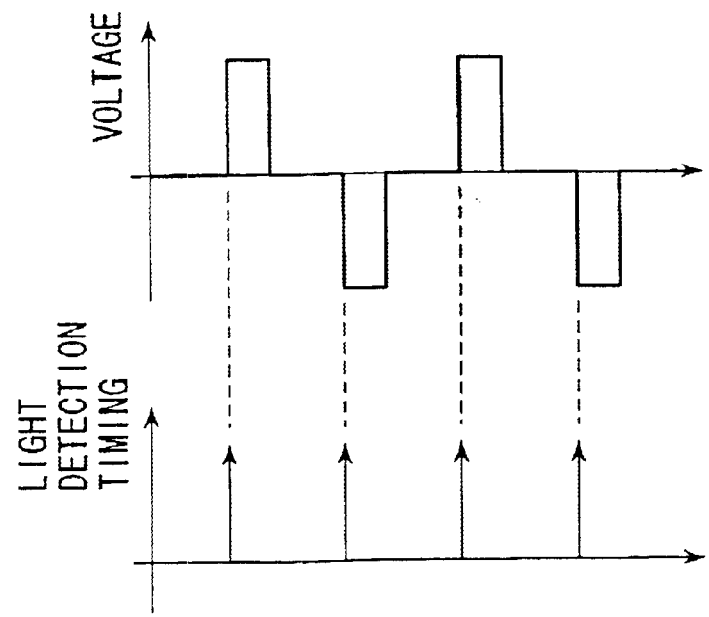
FIG. 11A
FIG. 11B

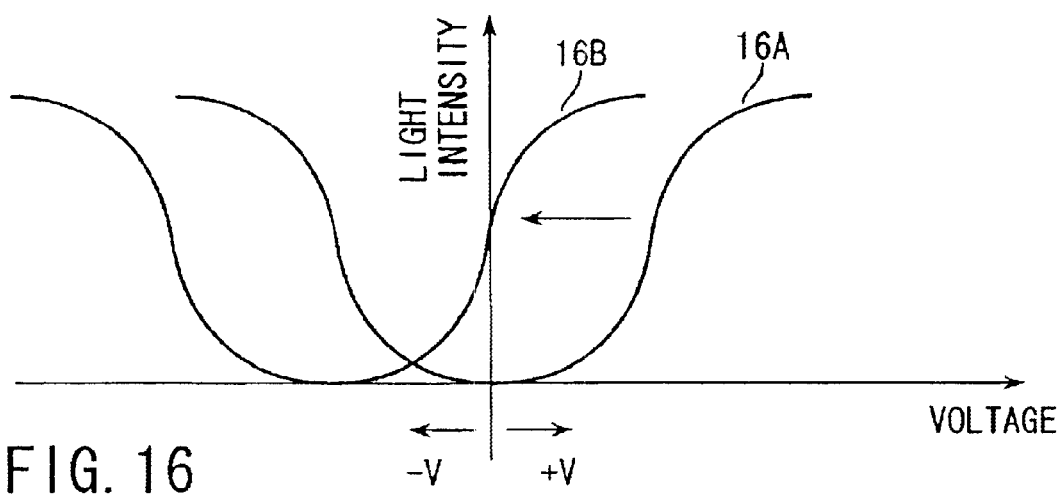
FIG. 16
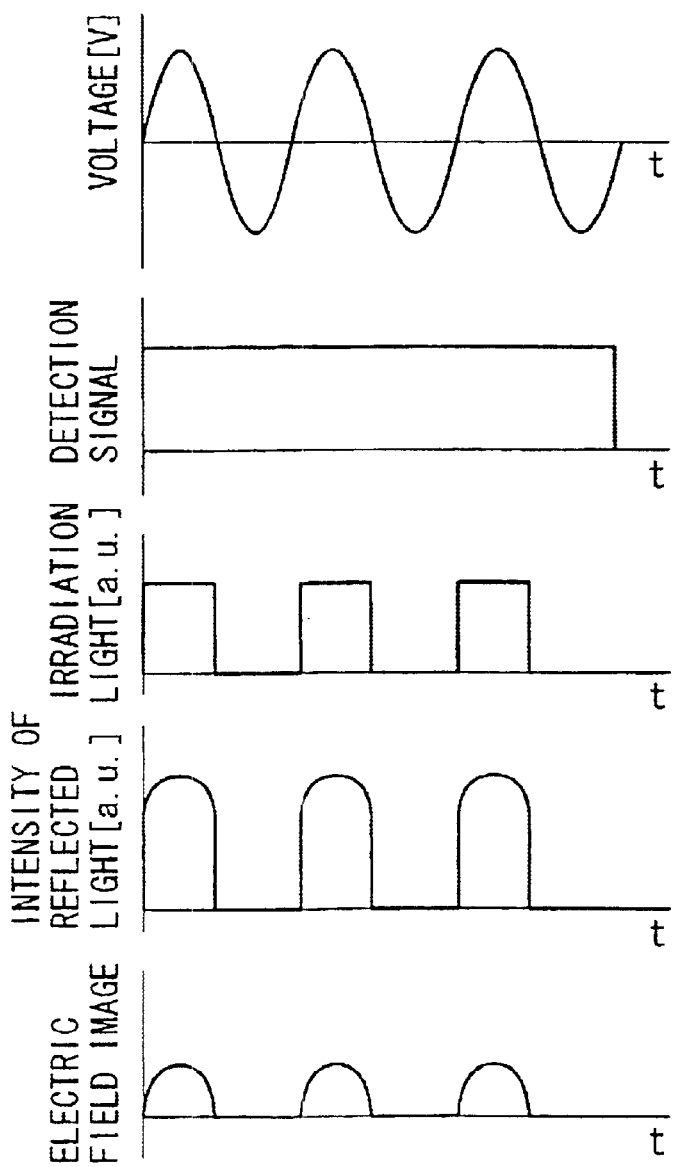
FIG. 17A
FIG. 17B
FIG. 17C
FIG. 17D
FIG. 17E

CIRCUIT PATTERN DETECTING APPARATUS AND CIRCUIT PATTERN INSPECTING METHOD

This application is a continuing application, filed under 35 U.S.C. §111(a), of International Application PCT/JP01/10478, filed Nov. 30, 2001, it being further noted that foreign priority benefit is based upon Japanese Patent Application 2000-366788 filed Dec. 1, 2000 and JP 2001-313771 filed Oct. 11, 2001.

BACKGROUND OF THE INVENTION

1. Field of the Invention

The present invention relates to a circuit pattern detecting apparatus and a circuit pattern inspecting method, which optically check the circuit pattern of a circuit board.

2. Description of the Related Art

As a conventional technique for checking whether the circuit pattern on a circuit board contains a disconnected or short-circuited portion, a technique that uses a dedicated jig is known. The jig is formed by use of spring probes and the pads of the circuit pattern are simultaneously brought into electric contact with the jig. This technique is not suitable for inspecting recently-developed circuit patterns having an increased number of pads since a large number of spring probes, which are expensive, are needed and the manufacturing cost of jig is inevitably high. In addition, since the pads are arranged with high density, reliable physical contact with them is hard to attain. The pads may be damaged if sharp spring probes are brought into contact with them.

Furthermore, in some circuit boards, one pad is a junction from which different circuit patterns branch off and is therefore connected to a plurality of other pads. In this case, the time needed for inspecting disconnected or short-circuited circuit portions may be very long.

Furthermore, although many circuit patterns may be formed in layers in some circuit boards, the technique for bringing the spring probes into contact with the pads cannot detect disconnected or short-circuited portions in such circuit patterns.

Under the circumstances, a technique for optically detecting the voltage distribution in a circuit pattern has been desired. As a conventional technique which measures the voltage distribution in a circuit pattern by utilization of the electro-optic effect, Japanese Patent Publication (KOKAI) No. 9-72947 discloses a known solder connection detection method and detection apparatus for electronic parts. According to the publication, the electric field strength of a predetermined position is detected in a non-contact manner by means of an electro-optic sensor, and the solder connection state of the circuit board is examined. However, the method can detect only the electric field at the tip end of the electro-optic sensor, and the electro-optic sensor has to be scanned so as to obtain the voltage distribution of the entire circuit pattern.

On the other hand, Japanese Patent Publication (KOKAI) No. 5-256794 describes an apparatus which detects disconnected, short-circuited or other defective portions in a pixel electrode, gate wiring and source wiring of a liquid-crystal display panel, by measuring the voltage distribution in a non-contact manner. According to this publication, an electro-optic device located near the circuit board is irradiated with a collimated beam, and the voltage distribution in a circuit pattern is detected in two dimensions based on the reflected light.

However, since the index of birefringence of an electro-optic device is high, interference fringes are inevitably produced due to the interference between the light reflected by the obverse surface of the device and the light reflected by the reverse surface. As a result, a voltage distribution image based on the reflected light deteriorates significantly.

Moreover, when a voltage is applied to the circuit pattern of a circuit board, electric charges tend to diffuse in the plane direction of the electro-optic device, deteriorating the voltage distribution. In other words, when voltage is applied to the circuit pattern of the circuit board, the voltage distribution of the circuit pattern may undesirably spread to the electro-optic device, due to the DC resistance components in the plane direction, especially the DC resistance components which the reflecting layer of the electro-optic device may have.

An object of the present invention is to provide a circuit pattern detecting apparatus and a circuit pattern detecting method, which optically detect the voltage distribution of a circuit pattern on a circuit board with high accuracy and which inspect disconnected or short-circuited portions of the circuit pattern.

BRIEF SUMMARY OF THE INVENTION

An electro-optic device according to the present invention comprises:

an electro-optic crystal layer;

a transparent electrode layer located at a light-incidence side of the electro-optic crystal layer; and a reflection preventing layer located between the electro-optic crystal layer and the transparent electrode layer.

A circuit pattern detecting apparatus according to the present invention comprises:

an electro-optic device having the structure mentioned above and located near a circuit board on which a circuit pattern is formed;

an electric field generating circuit which generates an electric field in accordance with the circuit pattern and applies the electric field to the electro-optic crystal layer; and a detector which detects intensity distribution of reflected light reflected by the electro-optic device whose polarization plane changes in accordance with the index of birefringence which varies with the electric field.

An electro-optic device according to the present invention comprises:

an electro-optic crystal layer;

a transparent electrode layer located at an light-incidence side of the electro-optic crystal layer;

an adhesive layer located between the electro-optic crystal layer and the transparent electrode layer;

a first reflection preventing layer located between the electro-optic crystal layer and the adhesive layer; and a second reflection preventing layer located between the transparent electrode layer and the adhesive layer.

A circuit pattern detecting apparatus according to the present invention comprises:

an electro-optic device having the structure mentioned above and located near a circuit board on which a circuit pattern is formed;

an electric field generating circuit which generates an electric field in accordance with the circuit pattern and applies the electric field to the electro-optic crystal layer; and a detector which detects intensity distribution of reflected light reflected by the electro-optic device whose polarization plane changes in accordance with the index of birefringence which varies with the electric field.

A circuit pattern detecting method of the present invention comprises:

irradiating an electro-optic device with light, the electro-optic device being located near a circuit board on which a circuit pattern is formed, and including an electro-optic crystal layer, a transparent electrode layer located at a light-incidence side of the electro-optic crystal layer, and a reflection preventing layer located between the electro-optic crystal layer and the transparent electrode layer;

applying a voltage between the circuit board and the electro-optic crystal layer to generate an electric field, and changing the index of birefringence of the electro-optic crystal layer in accordance with the circuit pattern by utilization of the electric field; and detecting reflected light reflected by the electro-optic device, and detecting a voltage distribution pattern between the circuit board and the electro-optic crystal layer.

A circuit pattern detecting method of the present invention comprises:

irradiating an electro-optic device with light, the electro-optic device being located near a circuit board on which a circuit pattern is formed, and including an electro-optic crystal layer, a transparent electrode layer located at a light-incidence side of the electro-optic crystal layer, an adhesive layer located between the electro-optic crystal layer and the transparent electrode layer, a first reflection preventing layer located between the electro-optic crystal layer and the adhesive layer, and a second reflection preventing layer located between the transparent electrode layer and the adhesive layer;

applying a voltage between the circuit board and the electro-optic crystal layer to generate an electric field, and changing the index of birefringence of the electro-optic crystal layer in accordance with the circuit pattern by utilization of the electric field; and detecting reflected light reflected by the electro-optic device, and detecting a voltage distribution pattern between the circuit board and the electro-optic crystal layer.

A circuit pattern detecting apparatus according to the present invention comprises:

an electro-optic device located near a circuit board on which a circuit pattern is formed, and having a polarization plane that changes in accordance with the index of birefringence varying with the electric field;

a voltage application circuit which applies a periodic zero-sum voltage between the circuit pattern and the electro-optic device in order to apply the electric device with an electric field determined in accordance with the circuit pattern;

a light source which irradiates the electro-optic device with light; and a detector which detects the intensity distribution of reflected light reflected by the electro-optic device.

A circuit pattern inspecting apparatus according to the present invention comprises:

an electro-optic device located near a circuit board on which a circuit pattern is formed, and having a polarization plane that changes in accordance with the index of birefringence varying with the electric field;

a voltage application circuit which applies a voltage between the circuit pattern and the electro-optic device in order to apply the electric device with an electric field determined in accordance with the circuit pattern;

a light source which irradiates the electro-optic device with light; and a detector which detects the intensity distribution of reflected light reflected by the electro-optic device in synchronism with application of the voltage.

A circuit pattern detecting method according to the present invention comprises:

irradiating an electro-optic device with light, the electro-optic device being located near a circuit board on which a circuit pattern to be inspected is formed;

applying an AC voltage between the circuit board and the electric electro-optic crystal layer to generate an electric field, and changing the index of birefringence of the electro-optic crystal layer in accordance with the circuit pattern by utilization of the electric field; and detecting reflected light reflected by the electro-optic device when the AC voltage has a maximal amplitude, and detecting a voltage distribution pattern between the circuit board and the electric electro-optic crystal layer.

A circuit pattern detecting method according to the present invention comprises:

irradiating an electro-optic device with light, the electro-optic device being located near a circuit board on which a circuit pattern to be inspected is formed;

applying a pulse voltage between the circuit board and the electric electro-optic crystal layer to generate an electric field, and changing the index of birefringence of the electro-optic crystal layer in accordance with the circuit pattern by utilization of the electric field; and detecting reflected light reflected by the electro-optic device when the pulse voltage rises, and detecting a voltage distribution pattern between the circuit board and the electric electro-optic crystal layer.

A circuit pattern detecting apparatus according to the present invention comprises:

an electro-optic device located near a circuit board on which a circuit pattern is formed, and having a polarization plane that changes in accordance with the index of birefringence varying with an electric field;

a voltage application circuit which applies a voltage between the circuit pattern and the electro-optic device in order to apply the electric device with an electric field determined in accordance with the circuit pattern;

a light source which irradiates the electro-optic device with light;

a detector which detects the intensity distribution of reflected light reflected by the electro-optic device; and a control device which controls the light irradiation from the light source or the light incidence to the detector such that irradiation light or incidence light is changed into pulse light.

A circuit pattern detecting method according to the present invention comprises:

applying an AC voltage between a circuit board on which a circuit pattern to be inspected is formed, and an electro-optic device located near the circuit board, so as to generate an electric field, and changing the index of birefringence of the electro-optic crystal layer in accordance with the circuit pattern by utilization of the electric field;

irradiating the electro-optic device with pulse light in association with a cycle of the AC voltage; and detecting reflected light reflected by the electro-optic device, and detecting a voltage distribution pattern between the circuit board and the electric electro-optic crystal layer.

A circuit pattern detecting method according to the present invention comprises:

applying an AC voltage between a circuit board on which a circuit pattern to be inspected is formed, and an electro-optic device located near the circuit board, so as to generate an electric field, and changing the index of birefringence of the electro-optic crystal layer in accordance with the circuit pattern by utilization of the electric field;

irradiating the electro-optic device with light; and detecting reflected light reflected by the electro-optic device in association with a cycle of the AC voltage, and detecting a voltage distribution pattern between the circuit board and the electric electro-optic crystal layer.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 7 shows how electric charges diffuse in the planar direction when a step voltage is applied to the electro-optic device of the fourth embodiment;

FIGS. 8A and 8B show how an AC voltage is applied to the electro-optic device of the fourth embodiment;

FIGS. 11A and 11B illustrate how positive and negative pulse voltages are applied to the electro-optic device of a fifth embodiment;

FIG. 16 is a graph showing how the voltage and the light intensity are related to each other according to the ninth embodiment;

FIGS. 17A, 17B, 17C, 17D, and 17E illustrate how the circuit pattern detecting apparatus of a tenth embodiment of the present invention operates;

DETAILED DESCRIPTION OF THE INVENTION

Embodiments of the present invention will now be described with reference to the accompanying drawings.

Figure 1:
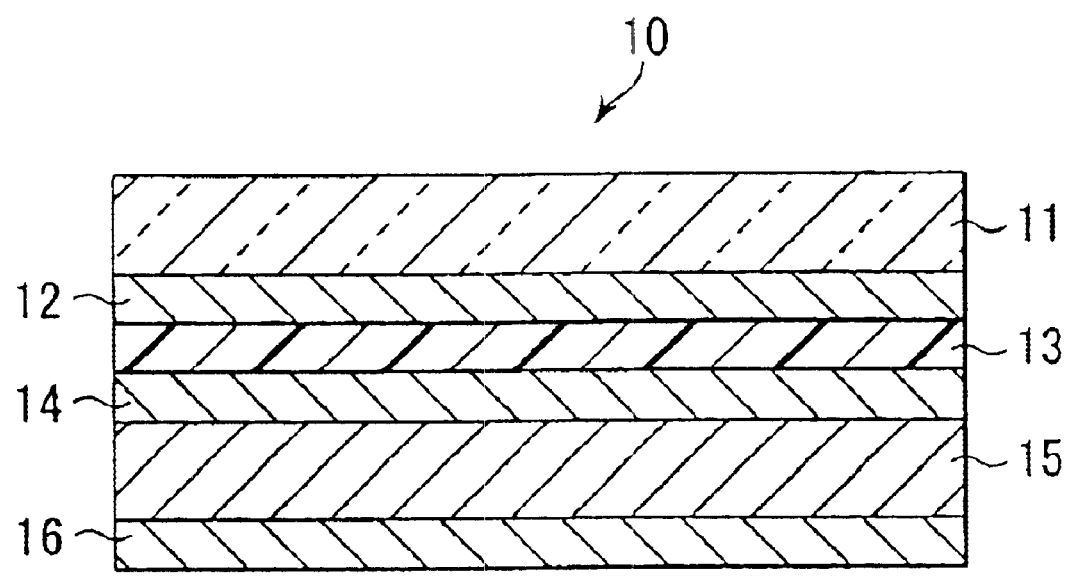
FIG. 1 is a sectional view showing the structure of an electro-optic device according to a first embodiment of the present invention.

FIG. 1 is a sectional view schematically showing an electro-optic device 10 according to the first embodiment of the present invention. A transparent conductive layer 12 is formed below a glass substrate 11. An electro-optic crystal layer 15, prepared independently, has a reflection preventing layer 14 and a reflecting layer 16 formed on its respective surfaces. The reflection preventing layer 14 of the independently-prepared electro-optic crystal layer 15 is attached to the (lower) surface of the transparent conductive layer 12 through an adhesive layer 13. In other words, the reflection preventing layer 14 is formed between the adhesive layer 13 and the electro-optic crystal layer 15.

The transparent conductive layer 12 serves as an electrode and is made of an ITO (Indium Tin Oxide) layer.

As the electro-optic crystal layer 15, a Pockels crystal or the like is known. Where the Pockels crystal detects an electric field through the use of light, two kinds of detection are known: one is lateral electric field detection which can sense an electric field in a direction perpendicular to light, and the other is longitudinal electric field detection which can sense the electric field in a direction parallel to the light. In order to correctly detect the electric field distribution in accordance with the voltage distribution generated in the circuit board, the longitudinal electric field detection is used. As the Pockels crystal enabling the longitudinal electric field detection which can sense an electric field in a direction parallel to the traveling direction of light, various kinds of crystals are known, including $Bi_{12}SiO_{20}$ (BSO, bismuth silicon oxide), GaAs (gallium arsenide), 55°-cut $LiNbO_3$, ZnSe, KDP ($KH_2PO_4$, potassium hydrogen phosphate), KTP ($KTiOPO_4$, potassium titanyl phosphate), BSO ($Bi_{12}SiO_{20}$, bismuth silicon oxide). KDP and KTP are deliquescent, and ZnSe, GaAs, etc. have a small electro-optic coefficient. It is therefore desirable to employ a BSO crystal which has a high index of birefringence and is not deliquescent, which is cubic and has an isotropic property, and which has a comparatively large electro-optic coefficient. For example, a BSO crystal whose size is in the range of about 1 to 30 mm is ground to have a thickness in the range of 100–500 μm, and the resultant layer is used as the electro-optic crystal layer 15. If the BSO crystal is less than 100 μm, the potential difference is small, so that the detection sensitivity of an electric field lowers. Conversely, if the BSO crystal exceeds 500 μm, the electric field spreads in the planar direction, as a result of which the detection of a voltage distribution is not easy.

The electro-optic crystal layer 15 of the electro-optic device 10 used in the present embodiment is not limited to the above-mentioned materials. It may be formed of any kind of material as long as its index of birefringence changes in response to the electric field. It may be any one of the materials mentioned above or selected from among the materials not mentioned above.

It is desirable that the electro-optic crystal layer 15 have its both surfaces subjected to optical polishing, and the planar aberration thereof be about (¼)λ (λ: wavelength). When used in a circuit board-detecting apparatus described later, the electro-optic crystal layer 15 should be so thin as to prevent an electric field from expanding between the circuit pattern of the circuit board and the transparent conductive layer 12. In this case, the electric field distribution is similar to the voltage distribution of the original circuit pattern. Therefore, in order to detect an electric field distribution which is similar in shape to the voltage distribution of the circuit pattern, the electro-optic crystal layer 15 should be thin. On the other hand, if the electro-optic crystal layer 15 is thin, and the electro-optic device 10 is set in a non-contact state at a position a predetermined distance away from the circuit pattern of the circuit board, the potential difference applied to the electro-optic crystal layer 15 is small in the capacitor structure between the circuit pattern and the transparent conductive layer 12. As a result, the detection sensitivity of an electric field lowers, and the working operation becomes hard to perform. Hence, the thickness of the electro-optic crystal layer 15 must be determined in consideration of the trade-off relations between these factors. In the present embodiment, the electro-optic crystal layer 15 has a thickness within the range of 100–500 mm μm.

The laser beam incident on the electro-optic device 10 (after passing through the glass substrate 11) is subjected to phase modulation by the electric field, and is reflected by the bottom surface of the electro-optic crystal layer 15. In many cases, the electro-optic crystal layer 15 has a high index of birefringence, and its reflection factor is also high. In the case where it is formed of $LiNbO_3$, the index of refraction is 2.2, and the reflection factor is about 14%. Therefore, the electro-optic crystal layer 15 may be optically polished to detect reflected light at the bottom surface. In order to further improve the reflection factor, the present embodiment forms a reflecting layer 16 on the bottom surface of the electro-optic crystal layer 15. The reflecting layer 16 is a dielectric multi-layered reflecting layer and is formed of $MgF_2$—$TiO_2$, $SiO_2$—$TiO_2$ or the like.

The electro-optic crystal layer 15 is thin and may be easily damaged. The electro-optic crystal layer 15 is therefore adhered to the glass substrate 11 on which the transparent conductive layer 12 is formed, through the use of the adhesive layer 13. If the adhesive layer 13 is formed of a material that significantly contracts when hardens, it is applied with a stress because the electro-optic crystal layer 15 is thin. In particular, if a dielectric crystal such as a bismuth silicon oxide (BSO) is used, it is likely that the optical characteristics will not be uniform. For this reason, the adhesive layer 13 is formed of a material that does not much contracts when hardens, such as an epoxy-based material.

The electro-optic device 10 has a multi-layered structure made up of materials of different indexes of refraction, as described above, and a laser beam incident on the electro-optic device 10 is highly coherent. As a result, interference caused by multiple reflection is likely to occur. The reflection factor is particularly large at the interface between the adhesive layer 13 and the electro-optic crystal layer 15 (which has a high index of refraction). For example, the index of refraction of the adhesive layer 13 is about 1.56 where this layer is formed of an epoxy-based adhesive, and the index of refraction of the electro-optic layer 15 is about 2.53 where this layer is formed of a bismuth silicon oxide (BSO). Because of this large difference in the indexes of refraction, interference fringes are generated by the reflection occurring on the upper and lower surfaces of the electro-optic crystal layer 15, and an image of a detected electric field distribution is significantly degraded thereby.

In the electro-optic device 10 of the first embodiment shown in FIG. 1, the reflection preventing layer 14, prepared in consideration of the difference between the indexes of refraction of the electro-optic crystal layer 15 and the adhesive layer 13, is provided between these layers. With this structure, the reflection factor at the upper surface of the electro-optic crystal layer 15 (the upper surface being a surface opposite to the reflecting layer 16) is reduced, and the interference fringes due to multiple reflection is suppressed. An image according to an electric field distribution can be detected reliably. The reflection preventing layer 14 has to be designed in consideration of the difference of the indexes of refraction between the adhesive layer 13 and the electro-optic crystal layer 15. In the present embodiment, the reflection preventing layer 12 is a multi-layered dielectric reflection preventing layer formed of $SiO_2$—$TiO_2$.

A description will be given of other embodiments of the present invention. In the descriptions below, the same reference numerals as in the first embodiment will be used to denote similar or corresponding structural elements, and a detailed description of such structural elements will be omitted herein.

Figure 2:
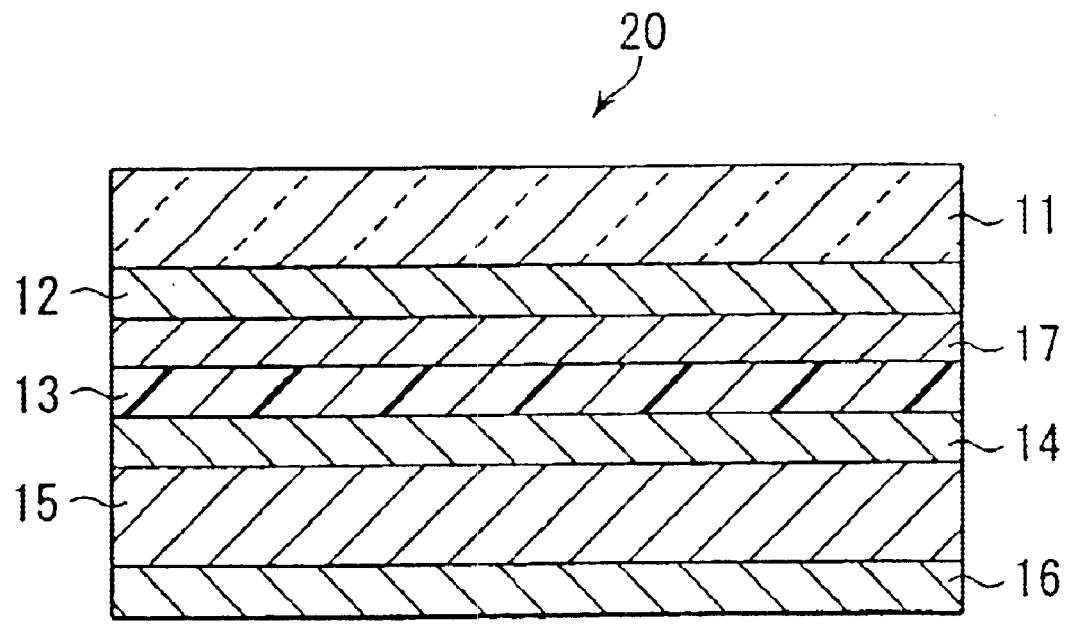
FIG. 2 is a sectional view showing the structure of an electro-optic device according to a second embodiment of the present invention.

FIG. 2 is a sectional view schematically showing an electro-optic device 20 according to the second embodiment. The second embodiment differs from the first embodiment in that a reflection preventing layer 17 is located between the transparent conductive layer 12 and the adhesive layer 13. With this structure, the reflection factor at the lower surface of the transparent conductive layer 12 (the lower surface being a surface opposite to the glass substrate 11) is decreased, and the quality of an image of the electro-optic crystal 20 is enhanced as a whole.

Since the index of refraction of the transparent conductive layer 12 is 1.90 and the index of refraction of the epoxy-based adhesive layer 13 is about 1.48, reflection occurs at the interface between them, leading to multiple reflection by the transparent conductive layer 12. In other words, like the reflection caused by the upper and lower surfaces of the electro-optic crystal layer 15 described in connection with the first embodiment, the transparent conductive layer 12 causes multiple reflection, and interference fringes may be generated. Therefore, the reflection preventing layer 17 is prepared in consideration of the difference between the index of refraction of the transparent conductive layer 12 and that of the adhesive layer 13.

According to the second embodiment, the reflection preventing layer 17 is formed between the electro-optic crystal layer 15 and the adhesive layer 13 as well. When the electro-optic device 20 is irradiated with a laser beam, the multiple reflection by the transparent conductive layer 12 as well as that by the electro-optic crystal layer 15 can be suppressed, and an electric field distribution can be detected as a satisfactory image.

Figure 3:
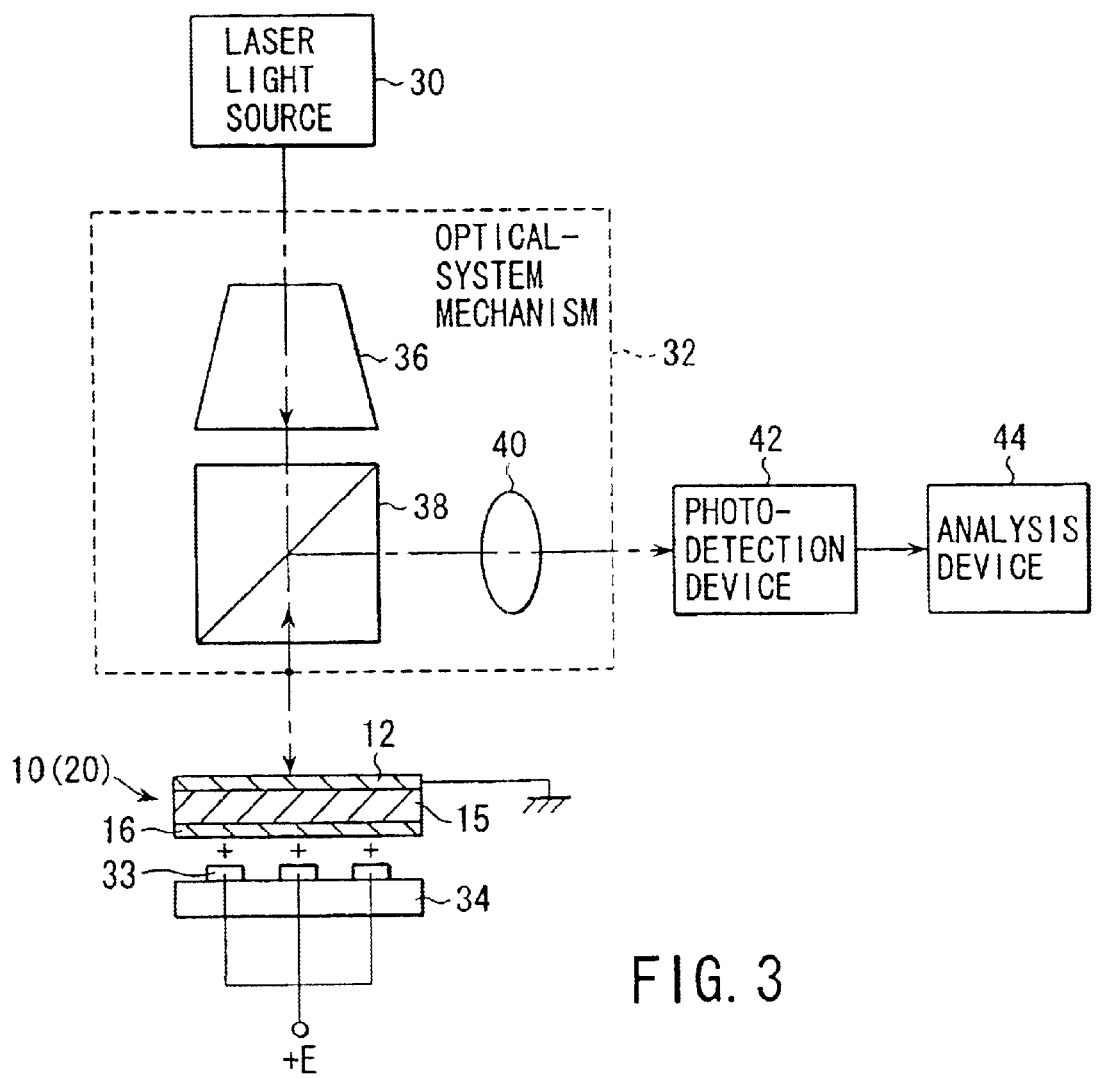
FIG. 3 is a schematic diagram showing the structure of a circuit pattern detecting apparatus according to a third embodiment of the present invention.

With reference to FIG. 3, a circuit pattern detecting apparatus using the electro-optic device 10 or 20 of the first or second embodiment will be described as the third embodiment. Light emitted by a laser light source 30 is incident on the electro-optic device 10 or 20 by way of an optical-system mechanism 32. Under the electro-optic device 10 or 20, a circuit board 34 on which a circuit pattern 33 is formed is located. The optical-system mechanism 32 includes a beam expander 36, a polarizing beam splitter 38 and an optical lens 40.

The laser light source 30 may be replaced with another type of light source, such as a halogen light source or a meta-halide light source.

The laser beam emitted by the laser light source 30 and guided toward the electro-optic device 10 or 20 is first incident on the beam expander 36, by which the laser beam is changed into a two-dimensional laser beam. This laser beam is polarized by the polarizing beam splitter 38 and is then guided to the electro-optic device 10 or 20.

Although the circuit board 34 is under the electro-optic device 10 or 20 in the neighborhood thereof, it may be in contact with the electro-optic device 10 or 20. Where the circuit board 34 and the electro-optic device 10 or 20 are not in contact, they are spaced from each other by a distance of about 20 $\mu$m. The transparent conductive layer 12 of the electro-optic device 10 or 20 is grounded, and an electric field is generated between the circuit pattern 33 and the transparent conductive layer 12 by applying a voltage to the circuit pattern 33. The index of birefringence of the electro-optic crystal layer 15 changes in accordance with the intensity of the electric field. As will be described later with reference to FIG. 10, the circuit pattern may be grounded, and a voltage may be applied to the transparent conductive layer 12 of the electro-optic device 10 or 20.

The plane of polarization of the light incident on the electro-optic device 10 or 20 changes in accordance with a change in the index of birefringence described above. The angle of polarization is determined by the electro-optic tensor of the electro-optic crystal 15 and the direction of the generated electric field vector. That is, the polarized state of the laser beam varies, depending upon the voltage distribution in the circuit pattern 33.

The laser beam reflected by the bottom surface (the reflecting layer 16) of the electro-optic device 10 or 20 also has its plane of polarization varied in accordance with a change in the index of birefringence of the electro-optic crystal layer 15.

The laser beam incident on the electro-optic device 10 or 20 is reflected by the bottom surface of the electro-optic crystal layer 15, and the reflected light is incident on the polarizing beam splitter 38. The laser beam reflected in the horizontal direction as viewed in the drawing has a light intensity whose distribution is determined in accordance with the electric field distribution.

A laser beam having a light intensity distribution determined in accordance with an electric field distribution can be condensed by an optical lens 40 and detected by a photo detection device 42. Hence, the voltage distribution of a circuit pattern can be detected as a two-dimensional light intensity distribution. A CCD or the like can be used as the photo detection device 42. The voltage distribution detected by the photo detection device 42 is analyzed and processed by an analysis device 44 (that is, the detected electric field intensity distribution is compared with a reference distribution). By this operation, defects (such as a disconnected portion and a short-circuited portion) of the circuit pattern 33 of the circuit board 34 can be inspected.

Since this detecting apparatus uses the electro-optic device 10 or 20 provided with the reflection preventing layers 14 and 17, the light source may be a laser light source 30 having a high degree of coherence. Even so, interference fringes, which are due to the multiple reflection by the electro-optic crystal layer 15, are not generated. In addition, the electric field distribution between the transparent conductive layer 12 and the circuit pattern 33 can be detected as a satisfactory image (which will be hereinafter referred to as an electric field image). Hence, the circuit pattern 33 of the circuit board 34 can be checked to locate defects, such as disconnected or short-circuited circuit portions, with sufficient accuracy.

The SN ratio can be improved by performing detection a number of times and averaging the results of detection.

Furthermore, stray light components can be decreased based on the detection result difference between a light irradiation time and a non-light irradiation time, as will be described later with reference to FIG. 9.

Figure 4A:
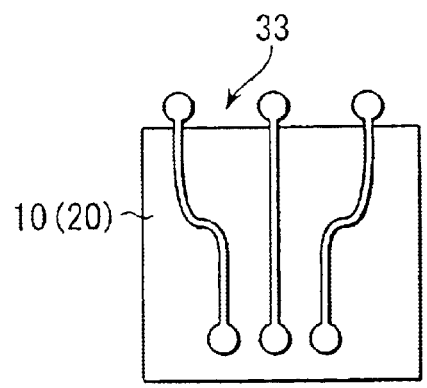
FIGS. 4A, 4B and 4C illustrate inspection principles underlying the third embodiment.
Figure 4B:
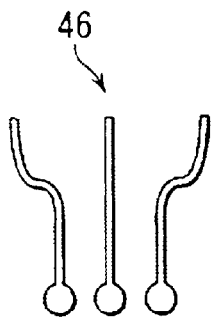
Figure 4C:
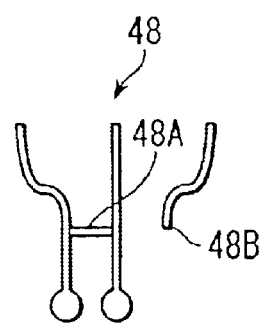

A description will be given with reference to FIGS. 4A–4C as to how disconnected or short-circuited portions of a circuit board are detected using an electric circuit image. Referring to FIG. 4A, electro-optic device 10 or 20 is disposed on the circuit pattern 33 (which is depicted as a pattern viewed from above). An electric field image 46 corresponding to a circuit pattern which has reliable electric characteristics faithfully reproduces the circuit pattern 33, as shown in FIG. 4B. On the other hand, an electric field image 48 corresponding to a circuit pattern which has defective electric characteristics contains a short-circuited portion 48A and a disconnected portion 48B, as shown in FIG. 4C. Therefore, the short-circuited portion 48A and the disconnected portion 48B can be detected by comparing the electric field images 46 and 48. The present invention is applicable not only to a circuit pattern formed on the obverse surface of a circuit board but also to a circuit pattern formed on the reverse surface or inside the circuit board.

According to the third embodiment, the detecting apparatus for checking the circuit pattern of the circuit board comprises an electro-optic device provided with a reflection preventing layer. Therefore, the intensity distribution of the electric field generated by a circuit pattern of a high-integrated circuit board can be accurately detected in a non-contact method utilizing the electro-optic effect, with the adverse effects by interference being suppressed. By comparing the detected electric field intensity distribution with the electric field intensity distribution of a non-defective circuit pattern, electric inspection can be performed in a short time by use of a simple positioning system.

In recent years, circuit boards are integrated with high density, and spring probes cannot be easily brought into contact with them. In many cases, therefore, the circuit boards are examined by visual inspection instead of checking them electrically. However, the visual inspection does not necessarily detects cracks or other defects in circuit patterns. According to the third embodiment, the voltage distribution of a circuit pattern is detected, with interference fringes suppressed. In other words, the intensity distribution of the electric field between an electro-optic crystal and a circuit pattern is detected as a satisfactory electric field image. Therefore, even defects (e.g., cracks) that cannot be detected by visual inspection can be detected.

Figure 5:
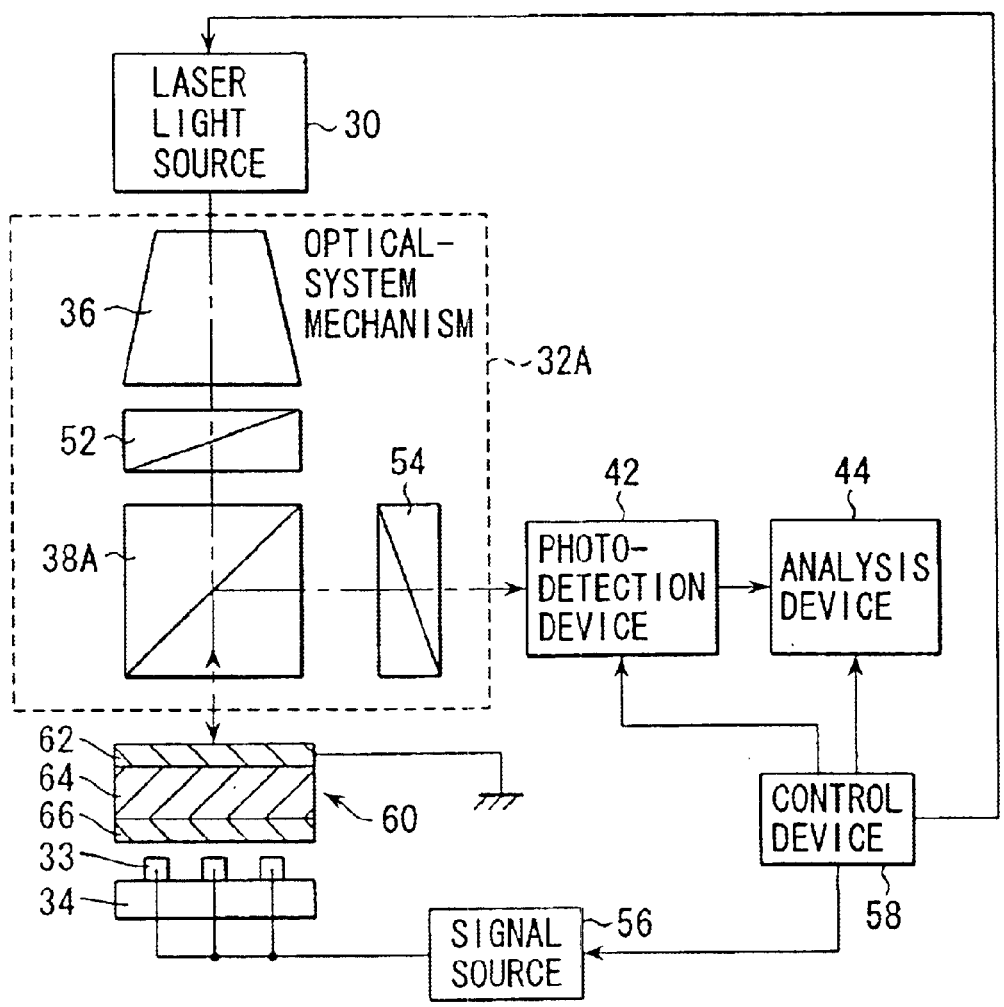
FIG. 5 is a schematic diagram showing the structure of a circuit pattern detecting apparatus according to a fourth embodiment of the present invention.

FIG. 5 shows a detecting apparatus according to the fourth embodiment. As shown, an optical-system mechanism 32A employs a beam splitter 38A in place of the polarizing beam splitter 38 of the third embodiment. A polarizer 52 is located between the beam expander 36 and the beam splitter 38A, and a photo detector 54 is used in place of the optical lens 40. A signal source 56 is connected to the circuit pattern 33 of the circuit board 34, and a voltage is applied to the circuit pattern 33 at timings determined by control signals supplied from a control device 58. The control device 58 also supplies control signals to the laser light source 30, photo detection device 42, and analysis device 44, and controls the light-irradiation, detection and analysis timings. The polarizer 52, beam splitter 38A, and photo detector 54 are equivalent to the polarizing beam splitter 38 of the third embodiment.

Although an electro-optic device 60 of the present embodiment may be like those 10 and 20 of the first and the second embodiments, an ordinary type of electro-optic device with no reflection preventing layer may be used instead. The electro-optic device 60 includes at least a transparent conductive layer 62, an electro-optic crystal layer 64, and a dielectric reflecting layer 66.

The laser light source 30 may be replaced with another type of light source, such as a halogen light source or a meta-halide light source. A laser beam emitted by the laser light source 30 and guided toward the electro-optic device 60 is first incident on the beam expander 36, by which the laser beam is changed into a two-dimensional laser beam. This laser beam is polarized by the polarizer 52 and is then guided to the electro-optic device 60.

A laser beam guided to the electro-optic device 60 is reflected by the dielectric reflecting layer 66, and has its polarization state changed in accordance with a change in the index of birefringence in the electro-optic crystal layer 64. The angle of polarization is determined by the electro-optic tensor of the electro-optic crystal 60 and the direction of the detected electric field vector. That is, the polarized state of the laser beam varies depending upon the voltage distribution in the circuit pattern 33.

With the plane of polarization changed, the laser beam from the electro-optic device 60 is incident on the beam splitter 38A. Of the laser beam, the perpendicularly branched components are supplied to the photo detector 54. The laser beam coming out of the photo detector 54 has a light intensity distribution determined in accordance with the voltage distribution of the circuit pattern 33. The photo detector 54 may be made of a polarizing plate or the like. By detecting the laser beam by use of the photo detection device 42, the voltage distribution of the circuit pattern 33 is detectable as a two-dimensional light intensity distribution. Defects, such as disconnected or short-circuited portions of the circuit pattern 33, can be inspected by analyzing and processing the voltage distribution detected by the photo detection device 42 by use of the analysis device 44.

From the standpoint of the electric characteristics, the electro-optic device 60 functions like a distributed constant circuit. The reactance component (capacity induction component) in the horizontal direction and the immittance component (DC resistance component) are negligible in an equivalent circuit. Therefore, this equivalent circuit can be depicted in such a way as is shown in FIG. 6.

Because of the capacitor component of the electro-optic crystal layer 64 formed between a reflecting layer 66 and the ITO layer 62, low-pass characteristics are present in the planar direction. Therefore, when the signal source 56 applies a step voltage to the circuit pattern 33, voltage $V_1$ is applied from this circuit pattern 33 to its neighboring capacitor component $C_1$ through the capacitor component $C_{air}$ of the air layer, as can be seen in FIG. 7. Likewise, voltages $V_2$, $V_3$ . . . $V_n$ are sequentially applied to the capacitor components $C_2$, $C_3$ . . . $C_n$, which are apart from one another in the planar direction. Thus, if a DC voltage is applied to the circuit pattern 33, the voltage distribution is detected as being spread, and the circuit distribution is undetectable.

The hitherto-known problem is that the reflecting layer 66 is not an ideal dielectric element and has high resistance in practice. In some cases, this has been a factor adversely affecting the resolution of the voltage distribution of a circuit pattern. To be more specific, when a DC voltage is applied to the circuit pattern, electric charges diffuse in the planar direction because of the resistance component of a dielectric reflecting layer, and the spatial resolution of the voltage distribution lowers.

Figure 6:
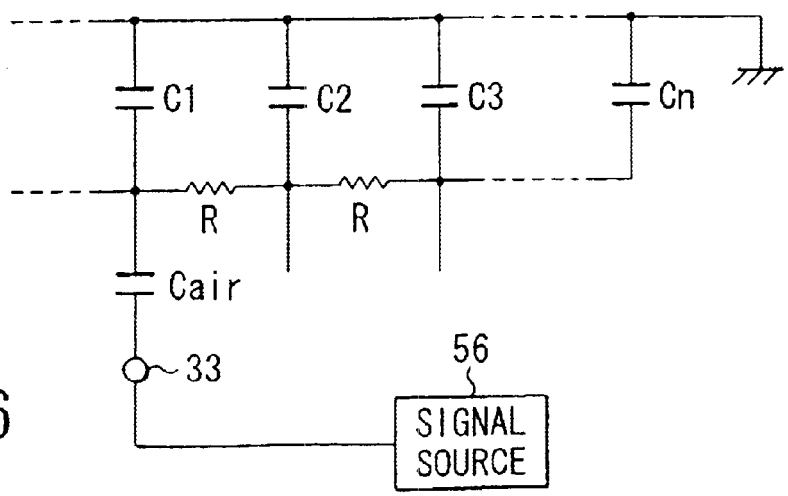
FIG. 6 is an equivalent circuit of the electro-optic device of the fourth embodiment.

As can be understood from the equivalent circuit shown in FIG. 6, application of an AC voltage to the circuit pattern serves to suppress the diffusion of electric charges in the planar direction and enables detection of the distribution of the voltage applied to the circuit pattern 33 with sufficient resolution.

In the present embodiment, the signal source 56 applies an AC voltage to the circuit pattern 33, as shown in FIG. 8A. In synchronism with the time when the absolute value of the AC voltage becomes maximal, the control device 58 controls the timing, and the photo detection device 42 detects the reflected light from the electro-optic device 60. When the absolute value of the AC voltage is large, the intensity of the detected voltage distribution also becomes large. For this reason, an AC voltage such as that shown in FIG. 11A is applied to the circuit pattern 33, and reflected light is detected in synchronism with the time when the amplitude of the AC voltage becomes maximal, as shown in FIG. 11B. As a result, the voltage distribution can be detected without being adversely affected by the distributed constant in the planar direction of electro-optic device 60.

Furthermore, the data on a plurality of light intensity distributions is detected in synchronism with the AC voltage, as shown in FIG. 8B. By averaging the light intensity distributions by use of the analysis device 44, the S/N ratio can be improved, and the voltage distribution can be detected as a light intensity distribution.

Figure 9:
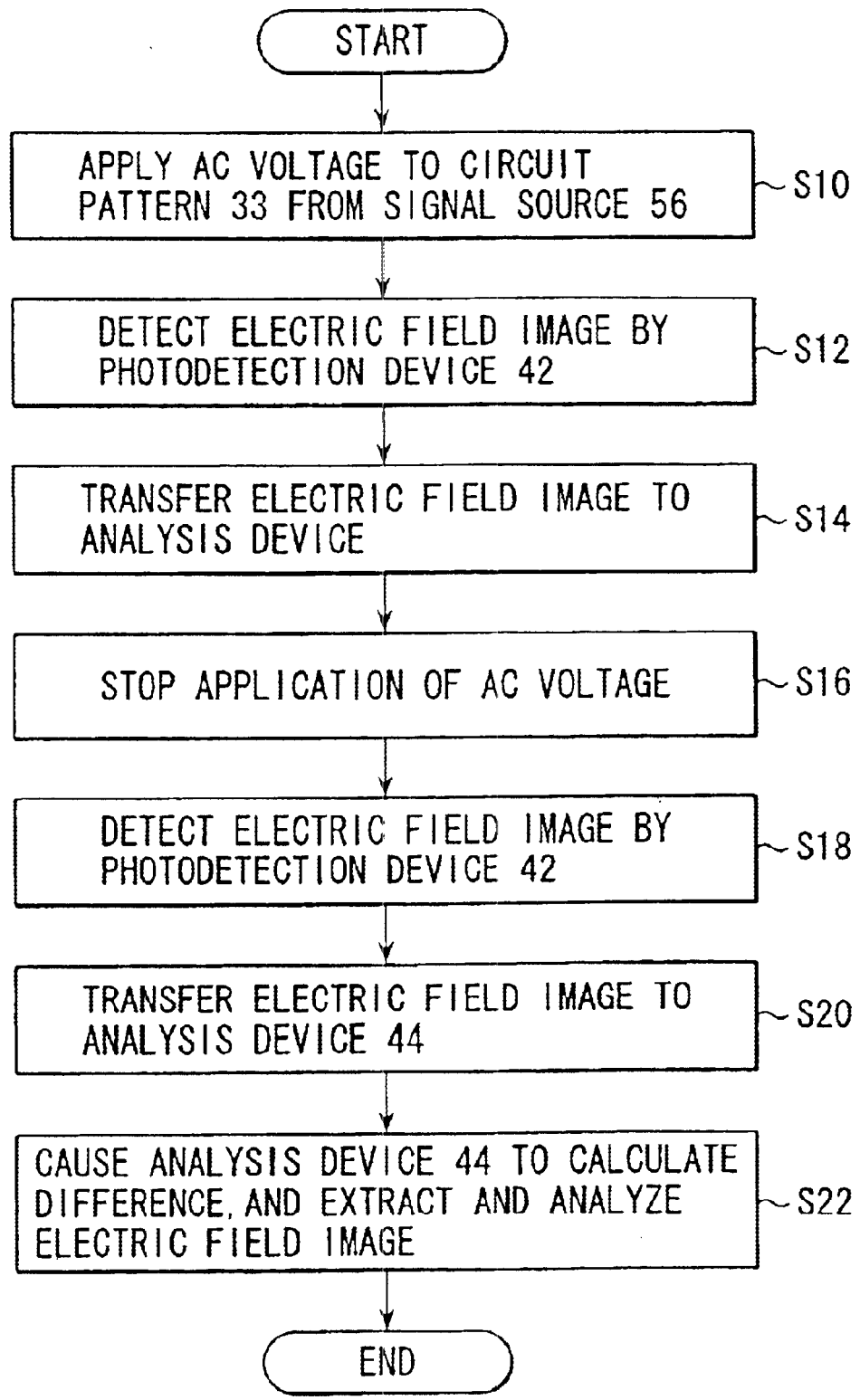
FIG. 9 is a flowchart illustrating the inspection routine according to the fourth embodiment.

FIG. 9 is a flowchart for illustrating how the detecting apparatus shown in FIG. 5 electrically inspects a circuit board on the basis of an electric circuit.

In Step S10, the control device 58 causes the signal source 56 to apply an AC voltage to the circuit pattern 33. As a result of this voltage application, an electric field distribution corresponding to the circuit pattern 33 is generated, and an electric field image having a shape corresponding to that of the electric field distribution becomes detectable by the photo detection device 42.

In Step S12, the control device 58 issues an image detection instruction and supplies it to the photo detection device 42. In response to this, the photo detection device 42 detects the electric field image.

In Step S14, the control device 58 issues an image transfer instruction and supplies this instruction to the photo detection device 42. In response to this, the photo detection device 42 sends the detected electric field image to the analysis device 44. Generally speaking, the photo detection device 42 inevitably detects a signal (a stray light component) produced by the extinction ratio of the polarizer 52 and the photo detector 54. Therefore, the stray light component is suppressed by detecting an image that corresponds only to the stray light component (i.e., an image that does not contain electric field components) and subtracting this image from the whole image.

In Step S16, therefore, the control device 58 causes the signal source 56 to stop application of the AC voltage to the circuit pattern 33, thereby detecting the stray light component.

In Step S18, the control device 58 issues an image detection instruction and supplies it to the photo detection device 42. In response to this, the photo detection device 42 detects the stray light image.

In Step S20, the control device 58 issues an image transfer instruction and supplies it to the photo detection device 42. Upon receipt of it, the photo detection device 42 sends the detected stray light image to the analysis device 44.

In Step S22, the stray light image detected in Step S18 is subtracted from the electric field image detected in Step S12, so as to obtain an electric field image free of the stray light component. The electric inspection of the circuit pattern is carried out by comparing that electric field with an electric field image corresponding to a reliable circuit pattern prepared beforehand.

Figure 10:
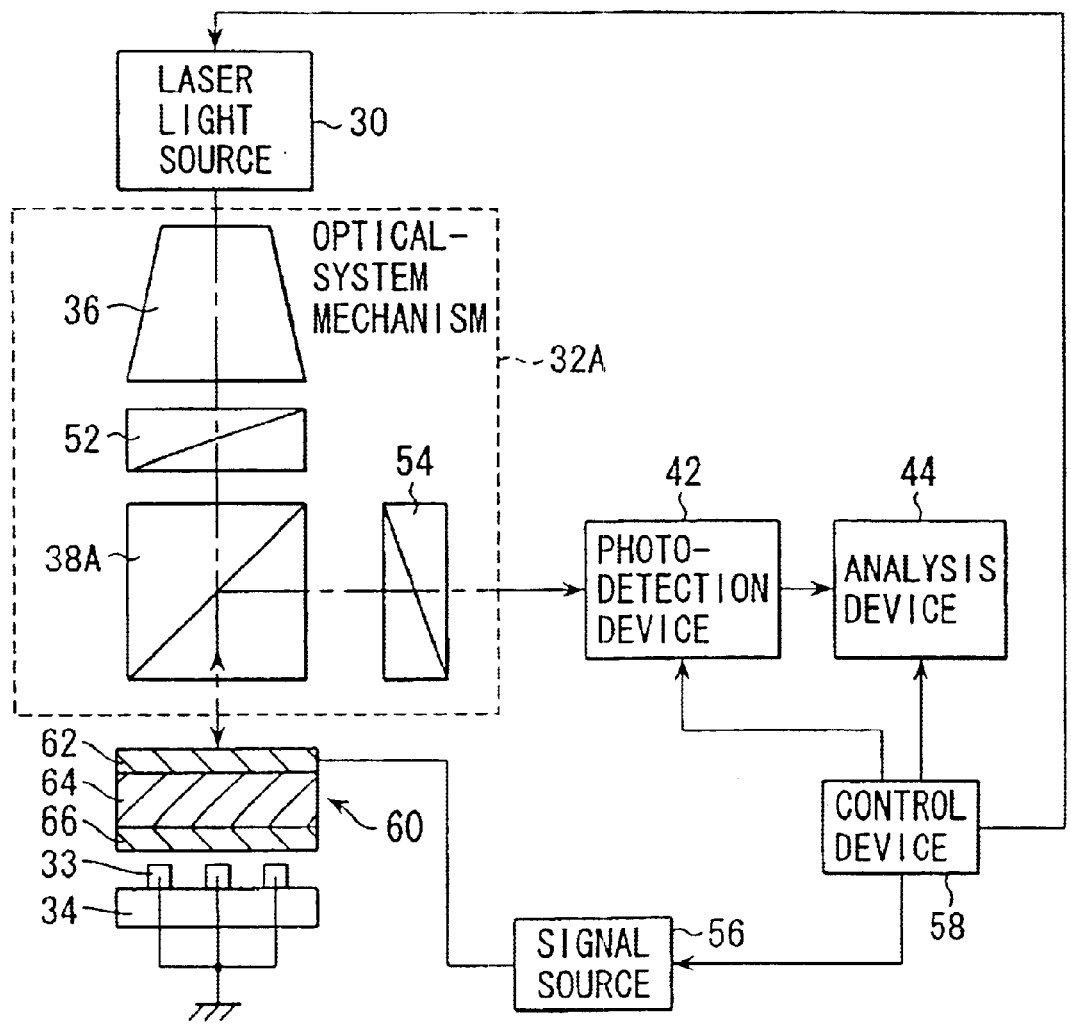
FIG. 10 is a schematic diagram showing a modification of the fourth embodiment.

The voltage for generating an electric field need not be applied to the circuit pattern 33; it may be applied to the transparent conductive layer 62 of the electro-optic device 60, as shown in FIG. 10. In other words, inspection similar to that described above is enabled by connecting the signal source 56 to the electro-optic device 60 (transparent electrode 62), not to the circuit board 34 (circuit pattern 33). Hence, the circuit pattern of the circuit board can be detected by means of a simple mechanism using a short bar or the like.

The detecting apparatus of the present embodiment detects the voltage distribution of the circuit pattern of the circuit board, using a method to which the electro-optic effect is applied. This detection can be performed without the spatial resolution being degraded by the distributed constant circuit characteristics in the planar direction of the electro-optic device. By analyzing the voltage distribution, it is possible to perform detection that contributes to reliable electric inspection of disconnected or short-circuited portions of highly-integrated circuit boards.

The detecting apparatus of the present embodiment can detect the voltage distribution of a circuit pattern as a two-dimensional field intensity distribution by merely arranging an electro-optic device on the circuit pattern of the circuit board. The detected field intensity distribution is compared with a field intensity distribution of the circuit pattern having satisfactory characteristics, and determination is made based on the comparison. Hence, electric inspection can be carried out by use of a simple positioning system and at a high detection speed.

The detecting apparatus of the present embodiment applies a periodic zero-sum voltage, e.g., an AC voltage, to a circuit pattern of a circuit board, for the purpose of detection. When the voltage is applied to the circuit pattern of the circuit board, the voltage distribution of the circuit pattern of the circuit board does not spread to an electro-optic device despite the DC resistance component in the planar direction, especially the DC resistance component the reflecting layer of an electro-optic device. Hence, the voltage distribution can be detected with a sufficient spatial resolution. None of the prior art technologies have paid attention to the fact that the DC resistance component of a dielectric reflecting layer causes electric charges to diffuse in the planar direction, adversely affecting the voltage distribution. In the present embodiment, the spatial resolution of the voltage distribution is improved by applying the periodic zero-sum voltage (e.g., an AC voltage) to the circuit pattern of the circuit board. The periodic zero-sum voltage is a voltage whose value becomes zero when subjected to periodic integration, and which does not include a DC component. It should therefore be noted that the periodic zero-sum voltage is not limited to the AC voltage. Instead of this, positive and negative voltages may be periodically applied.

FIGS. 11A and 11B illustrate the outline of the fifth embodiment wherein pulse voltages are applied as a periodic zero-sum voltage.

As shown in FIG. 11A, positive and negative pulses having the same amplitude are applied to the circuit pattern 33 from the signal source 56. As shown in FIG. 11B, in synchronism with the application timing of the pulse voltages, the control device 58 controls the timing, and the photo detection device 42 detects the light reflected from the electro-optic device 60. As a result, the voltage distribution can be detected with an improved resolution and at a high S/N ratio.

In the fourth and the fifth embodiments described above, the diffusion of electric charges in the planar direction is suppressed by application of a periodic zero-sum voltage. In the embodiments described next, an instantaneous waveform voltage is applied, and an electric field distribution is detected in the transitional stage when the electric field distribution is still present though the DC component of that voltage disappears the electric field distribution. Based on this detection, the diffusion of electric charges in the planar direction is suppressed in the embodiment.

Figure 12A:
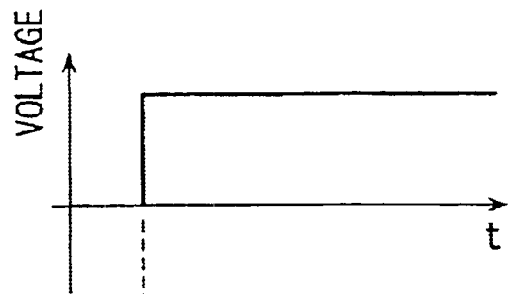
FIGS. 12A and 12B illustrate how a step voltage is applied to the electro-optic device of a sixth embodiment.
Figure 12B:
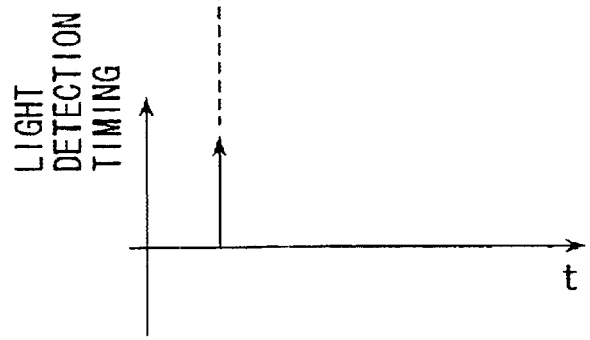

In the sixth embodiment, the signal source 56 applies a step voltage to the circuit pattern 33, as shown in FIG. 12A. As shown in FIG. 12B, in synchronism with the application timing of the step voltage, the control device 58 controls the timing, and the photo detection device 42 detects the light reflected from the electro-optic device 60. As a result, the voltage distribution can be detected as a light intensity distribution without being affected by the diffusion of electric charges in the electro-optic device 60.

Figure 13A:
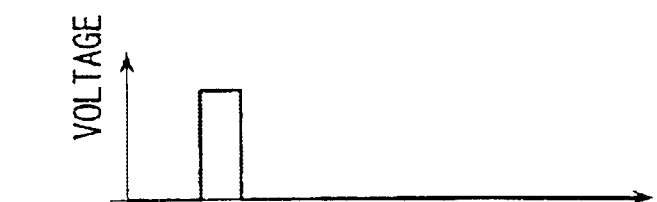
FIGS. 13A and 13B illustrate how a single pulse voltage is applied to the electro-optic device of a seventh embodiment.
Figure 13B:
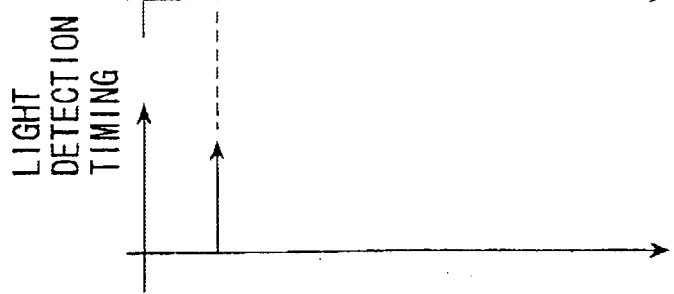

In the seventh embodiment, the signal source 56 applies a pulse voltage to the circuit pattern 33, as shown in FIG. 13A. As shown in FIG. 13B, in synchronism with the application timing of the pulse voltage, the control device 58 controls the timing, and the photo detection device 42 detects the light reflected from the electro-optic device 60. As a result, the voltage distribution can be detected as a light intensity distribution with an improved resolution without being affected by the diffusion of electric charges in the electro-optic device 60.

Figure 14A:
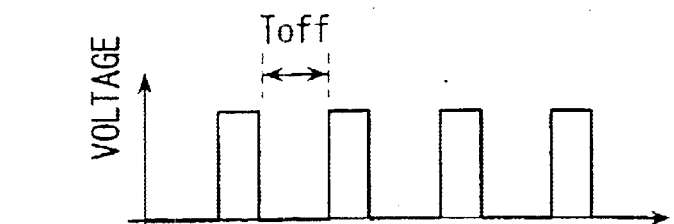
FIGS. 14A and 14B illustrate how a plurality of pulse voltages are applied to the electro-optic device of an eighth embodiment.
Figure 14B:
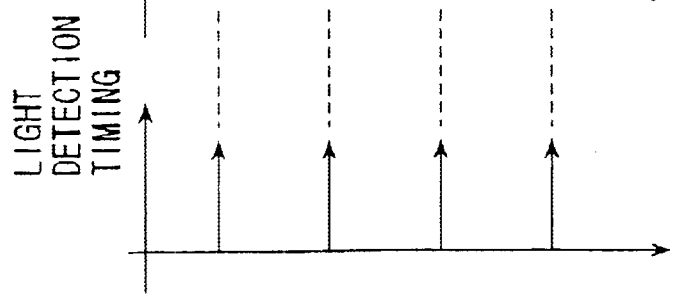

In the eighth embodiment, the signal source 56 successively applies pulse voltages to the circuit pattern 33, as shown in FIG. 14A. In synchronism with the application timing of the pulse voltages, the control device 58 controls the timing, and the photo detection device 42 detects the light reflected from the electro-optic device 60, as shown in FIG. 14B. At the time, the period $T_{off}$ in which no voltage is applied is set to be long enough to release the electric charges from the capacitor component of the electro-optic crystal layer 60. Hence, the voltage distribution is detectable as a light intensity distribution with an improved resolution without being affected by the electric charges in the electro-optic device 60. In this case as well, data on the light intensity distributions, which the photo detection device 42 detects in synchronism with successively-applied pulse voltages, are averaged by use of the analysis device 44. By this averaging operation, the voltage distribution can be detected as a light intensity distribution with an improved S/N ratio.

According to the sixth to eighth embodiments, reflected light is detected in an instant when a voltage is applied to the circuit pattern. Therefore, the voltage distribution of the circuit pattern can be detected with an improved spatial resolution before the voltage distribution spreads in the planar direction of the electro-optic device.

Figure 15:
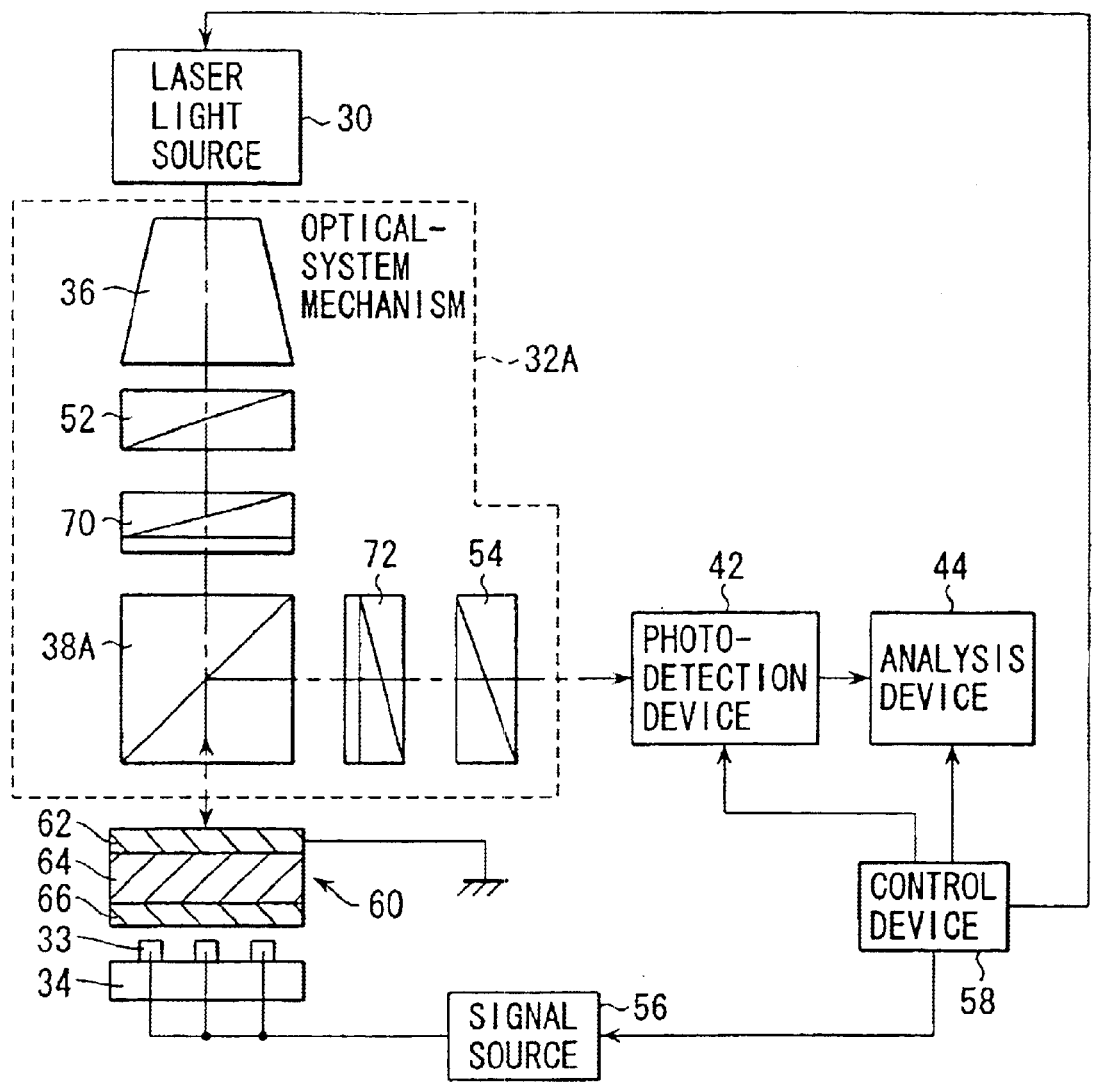
FIG. 15 is a schematic diagram showing a circuit pattern detecting apparatus according to a ninth embodiment of the present invention.
Figure 18:
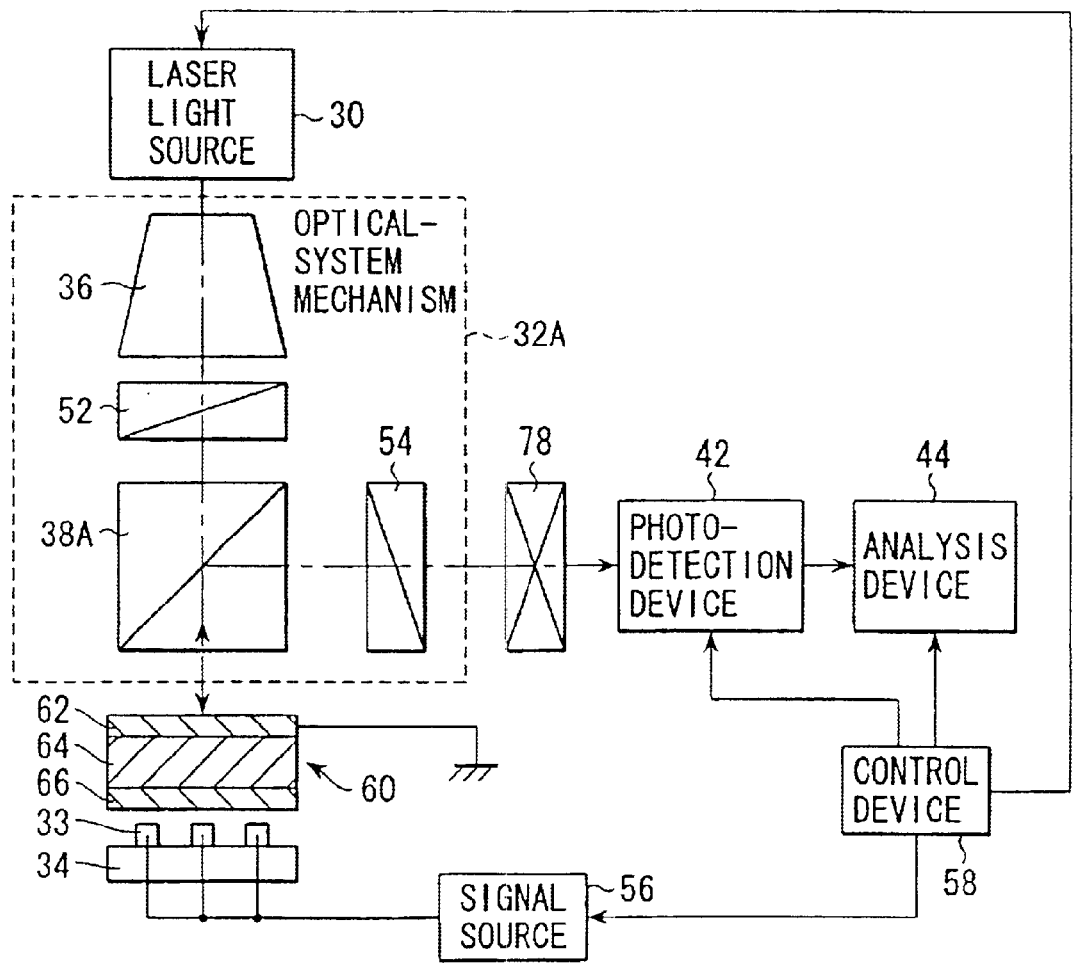
FIG. 18 is a schematic diagram showing a modification of the circuit pattern detecting apparatus of the tenth embodiment of the present invention.

FIG. 15 is a schematic diagram showing a circuit pattern detecting apparatus according to the ninth embodiment. The ninth embodiment differs from the first to eighth embodiments in that it employs a (⅛) wavelength plate 70 between the polarizer 52 and beam splitter 38A and another (⅛) wavelength plate 72 between the beam splitter 38A and photo detector 54. In the case where the latter (⅛) wavelength plate 72 is not provided, the former (⅛) wavelength plate 70 may be replaced with a (¼) wavelength plate. With this structure, a phase difference which is up to ¼ of one wavelength can be provided between the plane of polarization of the light incident on the electro-optic device 60 and that of the light coming out from the electro-optic device 60. When a voltage is applied to the circuit pattern 33, the relationship between the applied voltage and the light intensity changes from "16A" to "16B", as indicated in FIG. 16. The sensitivity is higher when the voltage is applied than when it is not.

As shown in FIG. 8A, an AC voltage is applied to the circuit pattern 33. As shown in FIG. 8B, in synchronism with the timing at which a positive voltage and a negative voltage are applied, the photo detection device 42 detects a light intensity distribution by controlling the timing with the control device 58. The analysis device 44 examines how the light intensity distribution differs between the time when the positive voltage is applied and the time when the negative voltage is applied. Based on this difference, the voltage distribution can be detected as a light intensity distribution with high sensitivity and with a high resolution.

The tenth embodiment will now be described. The apparatus according to this embodiment is similar to that of the fourth embodiment shown in FIG. 5.

The hitherto-known problem is that the reflecting layer 66 is not an ideal dielectric element and has high resistance in practice. In some cases, this has been a factor adversely affecting the resolution of the voltage distribution of a circuit pattern. To be more specific, when a DC voltage is applied to the circuit pattern because of the resistance component of a dielectric reflecting layer, electric charges diffuse in the planar direction, and the spatial resolution of the voltage distribution lowers. To solve this problem, an AC voltage is applied in the fourth embodiment.

Light-intensity changes caused by the electro-optic effect exhibit a nonlinear characteristic. Where the applied voltage and the light-intensity change are symmetrical with respect to the polarity of the voltage, the sensitivity is low in the neighborhood of 0V. However, where a phase difference is provided between the plane of polarization of the light incident on the electro-optic device 60 and that of the light coming out from it, as in the ninth embodiment, the relationships between the applied voltage and the light intensity become asymmetrical, as shown in FIG. 16. Because of this asymmetry, the sensitivity is high in the neighborhood of 0V. When an AC voltage is applied, however, the light intensity increases or decreases in response to the positive or negative voltage. Therefore, if a two-dimensional photo detection device such as a CCD is used for detection, the light-intensity changes in a detection cycle may be averaged, resulting in low sensitivity.

The tenth embodiment uses a pulse beam and detects its reflected light. Since the light-intensity change caused by application of an AC voltage is detected when the pulse light is being emitted, the voltage distribution of a circuit pattern can be detected with high sensitivity.

An operation of the tenth embodiment will be described with reference to FIG. 17A to FIG. 17E.

The control device 58 applies an AC voltage, such as that shown in FIG. 17A, to the circuit pattern 33 by controlling the signal source 56. The control device 58 continuously supplies a detection signal to the photo detection device 42, as shown in FIG. 17B. Unlike the fourth to ninth embodiments, the photo detection device 42 is in the state where reflected light is detectable at all times. As will be described later, however, the irradiation timing of light is controlled and light is emitted discretely, so that the photo detection device 42 discretely detects reflected light, as in the fourth to ninth embodiments. The light source of the embodiment emits pulse beams, but may emit continuous light instead. In this case, a shutter 78 is provided in the front of the photo detection device 42, so as to restrict the time in which the light is detected.

The control device 58 controls the light source 30 in such a manner that the electro-optic device 60 is irradiated with pulse light in synchronism with the positive or negative period of the AC voltage (the positive period in the illustrated case), as shown in FIG. 17C.

The pulse light is reflected by the dielectric reflecting layer 66, and the reflected light is detected by the photo detection device 42. On the reflected light, the light-intensity change component caused by the electric field generated by application of the AC voltage is superimposed. The intensity of the reflected light detected by the photo detection device 42 is shown in FIG. 17D. The light intensity detected by the photo detection device 42 reflects the intensity of the reflected light as long as the detection signal (FIG. 17B) of the photo detection device 42 is ON (namely, during the detection period). Therefore, the light-intensity change component (electric field image) caused by the electric field is extracted by subtracting the value corresponding to the emitted light from the detection result of the reflected light, as shown in FIG. 17E. Therefore, in the two-dimensional light intensity distribution detected by the photo detection device 42, a light-intensity change caused by the electric field is detected in the portion where the electric field generated from the circuit pattern exists. In this manner, the voltage distribution of the circuit pattern is obtained.

In the present embodiment as well, a stray light component can be canceled by measuring the intensity the reflected light has when no voltage is applied, and by subtracting the measured intensity from the intensity the reflected light has when a voltage is applied.

The eleventh embodiment will now be described with reference to FIG. 19A to FIG. 19G.

Figure 19A:
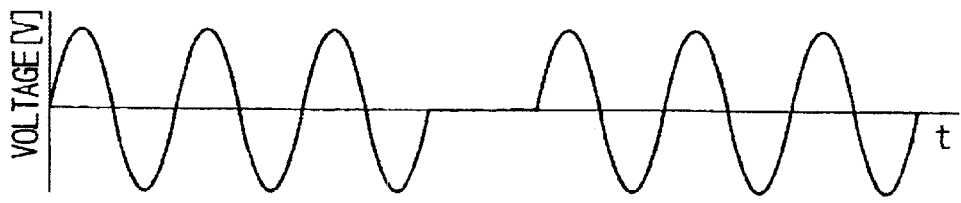
FIGS. 19A, 19B, 19C, 19D, 19E, 19F, and 19G illustrate how the circuit pattern detecting apparatus of an eleventh embodiment of the present invention operates.
Figure 19B:
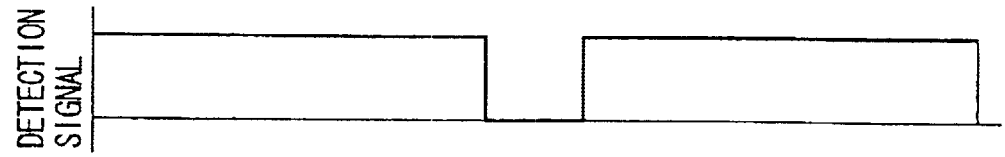

The control device 58 applies an AC voltage, such as that shown in FIG. 19A, to the circuit pattern 33 by controlling the signal source 56. The control device 58 continuously supplies a detection signal to the photo detection device 42, as shown in FIG. 19B.

Figure 19C:
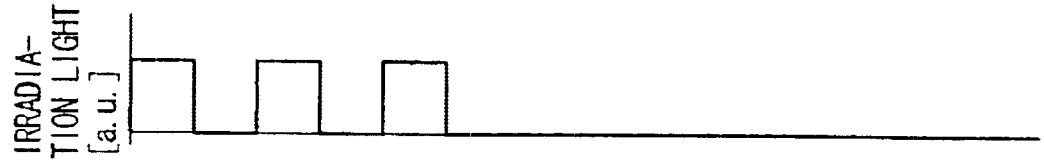

The control device 58 controls the light source 30 in such a manner that the electro-optic device 60 is irradiated with pulse light in synchronism with the positive period of the AC voltage, as shown in FIG. 19C.

Figure 19D:
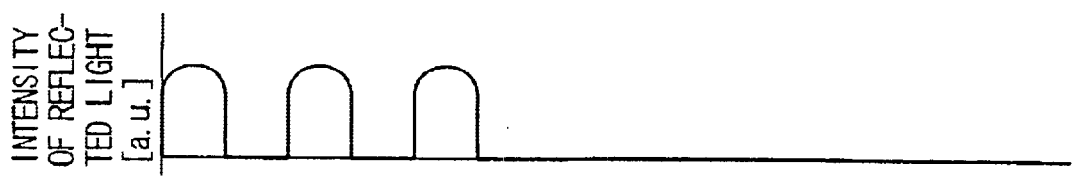

The pulse light is reflected by the dielectric reflecting layer 66, and the reflected light is detected by the photo detection device 42. On the reflected light, the light-intensity change component caused by the electric field generated by application of the AC voltage is superimposed. The intensity of the reflected light detected by the photo detection device 42 is shown in FIG. 19D. The light intensity detected by the photo detection device 42 reflects the intensity of the reflected light as long as the detection signal (FIG. 19B) of the photo detection device 42 is ON (namely, during the detection period). Therefore, the light-intensity change component (electric field image) caused by the electric field is extracted by subtracting the value corresponding to the emitted light from the detection result of the reflected light, as shown in FIG. 19G.

Figure 19E:

Next, the control device 58 controls the light source 30 in such a manner that the electro-optic device 60 is irradiated with pulse light in synchronism with the negative period of the AC voltage, as shown in FIG. 19E.

Figure 19F:
Figure 19G:

The pulse light is reflected by the dielectric reflecting layer 66, and the reflected light is detected by the photo detection device 42. On the reflected light, the light-intensity change component caused by the electric field generated by application of the AC voltage is superimposed. The intensity of the reflected light detected by the photo detection device 42 is shown in FIG. 19F. The light intensity detected by the photo detection device 42 reflects the intensity of the reflected light as long as the detection signal (FIG. 19B) of the photo detection device 42 is ON (namely, during the detection period). Therefore, the light-intensity change component (electric field image) caused by the electric field is extracted by subtracting the value corresponding to the emitted light from the detection result of the reflected light, as shown in FIG. 19G.

The detecting apparatus of the tenth or eleventh embodiment can detect the voltage distribution of a circuit pattern of a circuit board in a method to which the electro-optic effect is applied, and this detection can be performed with a high spatial resolution, while suppressing the adverse effects which may be caused when electric charges diffuse in the dielectric reflecting film of the electro-optic device. By analyzing the voltage distribution, electric inspection is performed to detect disconnected or short-circuited portions of highly-integrated circuit boards.

In the method of measuring a two-dimensional voltage distribution using the electro-optic effect, the spatial resolution of the voltage distribution deteriorates. This deterioration has been attributed to the phenomenon that the electric field generated from the circuit pattern inevitably spreads when it passes through the electro-optic crystal in the thickness direction thereof. As described above, however, the reflecting layer 66 is not an ideal dielectric element and has high resistance, and the this resistance is a factor affecting the resolution of the voltage distribution. This problem is not solved in any of the conventional methods which detect a voltage distribution by use of a two-dimensional photo detection device.

The method of the present invention applies an AC voltage to a circuit pattern at the time of detection. Because of this voltage application, the characteristics described above are improved, and a distribution can be detected with a high spatial resolution.

Changes in the light intensity distribution, caused by the electro-optic effect, exhibit nonlinear characteristics. In the configuration shown in FIG. 15, a phase compensation is provided between the plane of polarization of the light incident on the electro-optic crystal and that of the light coming out from it. Without this phase compensation, the polarities of the applied voltage and the light intensity exhibit symmetrical characteristics ("16A" in FIG. 16), in which case the sensitivity is markedly poor in the neighborhood of 0V. To make the characteristics asymmetrical, therefore, it is desirable that the phase difference be provided.

The sampling frequency of a CCD which is often used as a two-dimensional photo detection device, is 30 Hz. If an AC voltage higher than the Nyquist frequency of that sampling frequency is applied, changes in the light intensity, which increases or decreases in the sampling period, may be cancelled, leading to a poor sensitivity.

In the tenth and the eleventh embodiments, pulse light is emitted in synchronism with either positive or negative phase of an AC voltage. Since the light intensity is detected only when it is increased or decreased in accordance with an electric field, an AC voltage far higher than a Nyquist frequency can be applied, and the spatial resolution of the electric field increases.

Since the detection timing of an AC voltage and that of the photo detection device are asynchronous, the system configuration can be simple, accordingly. In addition, since the difference in voltage distribution is utilized, the voltage-applied portions of the circuit pattern can be detected with high sensitivity.

Figure 20:
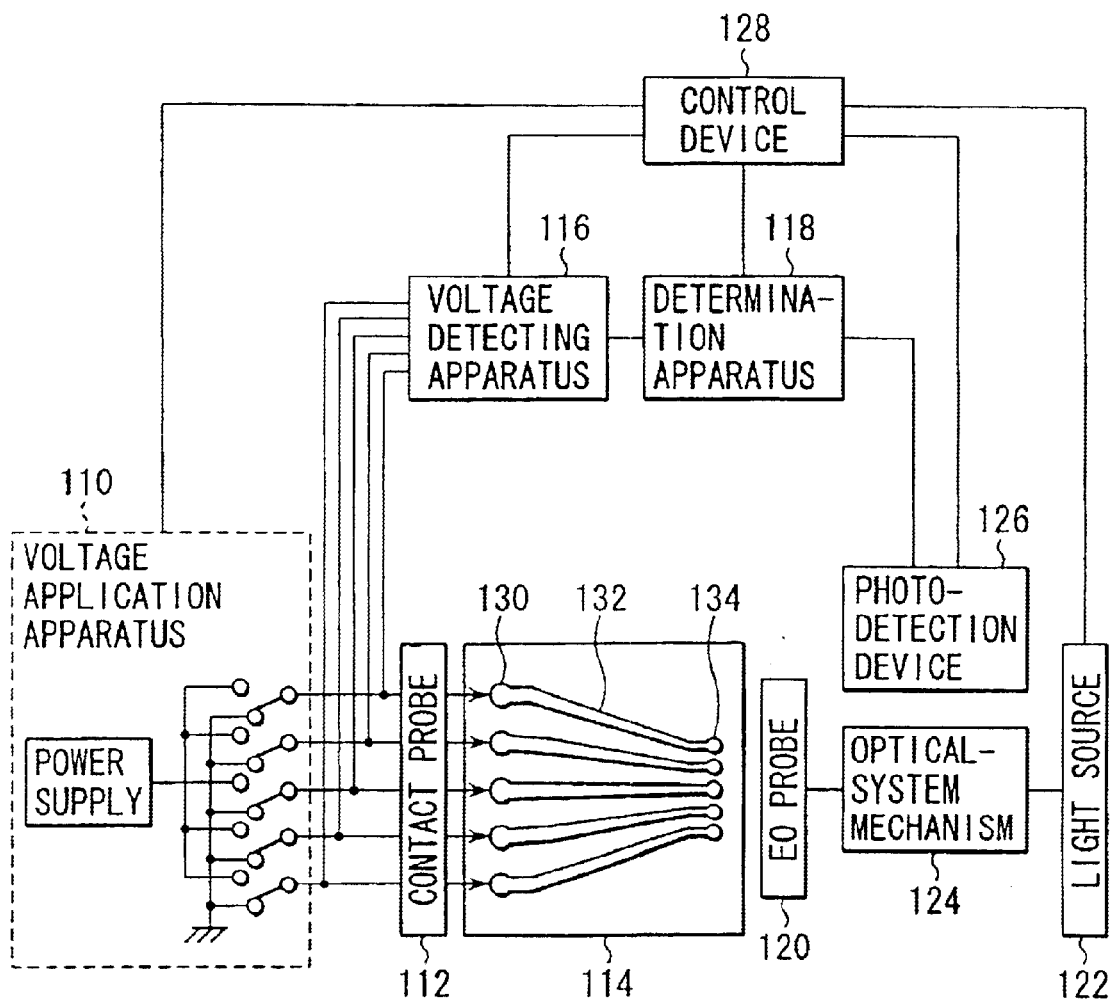
FIG. 20 schematically shows a circuit pattern detecting apparatus according to a twelfth embodiment of the present invention.

FIG. 20 shows an outline of the detecting apparatus of the twelfth embodiment. This embodiment includes a voltage application apparatus 110, contact probes 112, circuit board 114, voltage detecting apparatus 116, determination apparatus 118, electro-optic probes (EO probes) 120, light source 122, optical-system mechanism 124, photo detection device 126, and control device 128.

First, the voltage application apparatus 110 applies a voltage to a predetermined one of large-pitch pads 130 of the circuit board 114 by way of a corresponding contact probe 112. At this time, the voltage detecting apparatus 116 detects a voltage at the other large-pitch pads 130, and the determination apparatus 118 examines the electric condition (short-circuited state) of the circuit pattern 132 of the circuit board 114.

Next, the electro-optic probes 120 are arranged at predetermined intervals in the neighborhood of small-pitch pads 134. The electro-optic probes 120 may be in contact with the pads 134 or with circuit patterns 132 near the pads 134. Also, the electro-optic probes 120 may be arranged in a non-contact manner, with a distance of about 20 mm maintained. Light from the light source 122 is polarized by the optical-system mechanism 124, and is then incident on the electro-optic probes 120.

When a voltage is applied to the large-pitch pad 130, the electro-optic probe 120 detects an electric field generated from the corresponding small-pitch pad 134 unless the corresponding circuit pattern 132 is disconnected. At the time, the polarized state of reflected light from the electro-optic probe 120 is changed by the electric field generated from the small-pitch pad 134. A polarization component, which is subjected to changes by the electric field, is modulated by the optical-system mechanism 124 and turned into a light-intensity change. This light-intensity change is detected by the photo detection device 126. An electric state (disconnected state) of a circuit pattern is checked by examining the light intensity by the determination apparatus 118.

The control device 128 controls the series of operations described above.

Figure 21A:
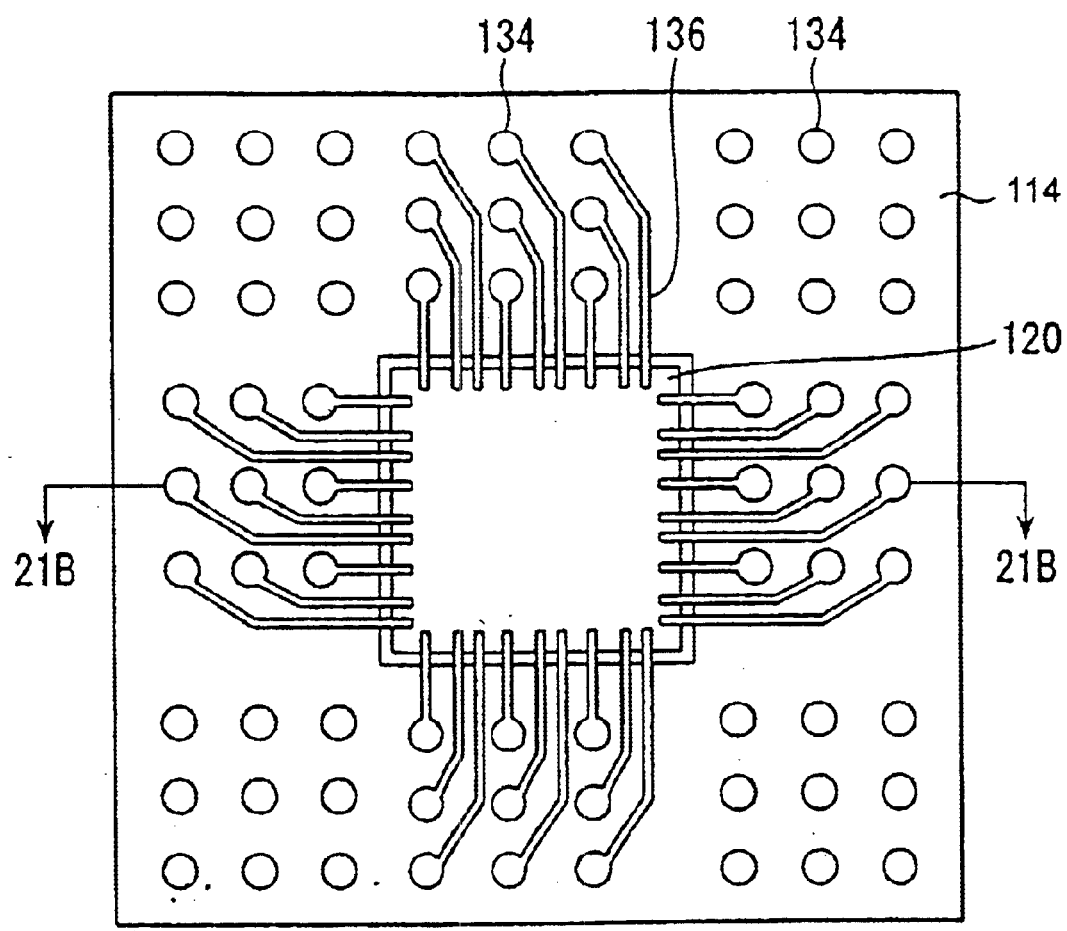
FIGS. 21A and 21B show an example of a manner in which inspection is carried out according to the twelfth embodiment.
Figure 21B:
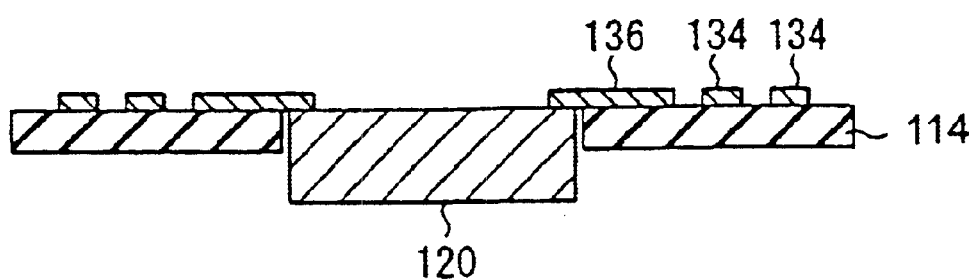

FIGS. 21A and 21B show an example of a manner in which inspection is carried out according to the embodiment. This inspection is intended to check the electric state (short-circuited/disconnected state) of a tape BGA (ball grid array), wherein pads 134 and circuit patterns 136 are formed on an insulating film 132. The electro-optic probes 120 are placed on the tip ends of the circuit patterns 136 of the tape BGA, and a voltage is applied from the pads 134. By so doing, the electric states (short-circuited and disconnected states) of the circuit patterns 136 can be inspected at a time without moving the electro-optic probes 120.

As electro-optic probe 120, an electro-optic device containing a reflection preventing layer shown in FIGS. 1 and 2 may be used. Alternatively, voltage application and pulse light irradiation, such as those described in relation to the fourth to eleventh embodiments, may be performed.

The present invention is not limited to the embodiments mentioned above. For example, the electro-optic crystal which is part of an electro-optic device may be replaced with an liquid crystal. In addition, the irradiation light need not be a laser beam but a non-laser beam. Furthermore, the embodiments described above do not have to be reduced to practice individually; they may be combined with one another, if need be.

As described above, the present invention can provide a circuit pattern detecting apparatus which optically detects the voltage distribution of a circuit pattern formed on a circuit board with high accuracy and which inspects disconnected or short-circuited portions of the circuit pattern. The present invention can also provide an electro-optic device used in the circuit pattern detecting apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A circuit pattern detecting apparatus comprising:
   an electro-optic device having an electro-optic crystal layer, a transparent conductive layer located at a light-incidence side of the electro-optic crystal layer, and a reflection preventing layer located between the electro-optic crystal layer and the transparent conductive layer, and located near a circuit board on which a circuit pattern is formed;
   an electric field generating circuit which generates an electric field in accordance with the circuit pattern and applies the electric field to the electro-optic crystal layer; and
   a detector which detects intensity distribution of reflected light reflected by the electro-optic device whose polarization plane changes in accordance with an index of birefringence which varies with the electric field.

2. A circuit pattern detecting apparatus according to claim 1, wherein the electric field generating circuit includes a signal source which causes the electro-optic device to be grounded and which applies an AC voltage to the circuit pattern.

3. A circuit pattern detecting apparatus according to claim 1, wherein the electric field generating circuit includes a signal source which causes the circuit pattern to be grounded and which applies an AC voltage to the electro-optic device.

4. A circuit pattern detecting apparatus according to claim 1, wherein the detector adds detection results obtained a number of times and calculates an average of the detection results.

5. A circuit pattern detecting apparatus according to claim 1, wherein the detector comprises: an analyzer which obtains a difference between the intensity distribution of the reflected light when light is incident on the electro-optic device end the intensity distribution of the reflected light when light is not incident on the electro-optic device and analyzes the circuit pattern in accordance with a difference between the intensity distributions.

6. A circuit pattern detecting method comprising:
   irradiating an electro-optic device with light, the electro-optic device being located near a circuit board on which a circuit pattern to be inspected is formed, and including an electro-optic crystal layer, a transparent conductive layer located at a light-incidence side of the electro-optic crystal layer, and a reflection preventing layer located between the electro-optic crystal layer and the transparent conductive layer; applying a voltage between the circuit board and the electro-optic crystal layer to generate an electric field, and changing the index of birefringence of the electro-optic crystal layer in accordance with the circuit pattern by utilization of the electric field; and
   detecting reflected light reflected by the electro-optic device, and detecting a voltage distribution pattern between the circuit board and the electro-optic crystal layer.

7. A circuit pattern detecting method comprising:
   irradiating an electro-optic device having an electro-optic crystal layer with two-dimensional light, the electro-optic device being located near a circuit board on which a circuit pattern to be inspected is formed;
   applying an AC voltage between the circuit board and the electro-optic crystal layer to generate an electric field, and changing an index of birefringence of the electro-optic crystal layer in accordance with the circuit pattern by utilization of the electric field; and
   detecting a two-dimensional light reflected by the electro-optic device when the AC voltage has a maximal amplitude, and detecting a voltage distribution pattern between the circuit board and the electro-optic crystal layer.

8. A circuit pattern detecting method comprising:
   irradiating an electro-optic device having an electro-optic crystal layer with two-dimensional light, the electro-optic device being located near a circuit board on which a circuit pattern to be inspected is formed;
   applying a pulse voltage between the circuit board and the electro-optic crystal layer to generate an electric field, and changing an index of birefringence of the electro-optic crystal layer in accordance with the circuit pattern by utilization of the electric field; and
   detecting a two-dimensional light reflected by the electro-optic device when the pulse voltage rises, and detecting a voltage distribution pattern between the circuit board and the electro-optic crystal layer.

9. A circuit pattern detecting apparatus comprising:

an electro-optic device located near a circuit board on which a circuit pattern is formed, and having a polarization plane that changes in accordance with an index of birefringence varying with an electric field;

a voltage application circuit which applies a periodic zero-sum voltage between the circuit pattern and the electro-optic device in order to apply the electro-optic device with an electric field determined in accordance with the circuit pattern;

a light source which irradiates the electro-optic device with light; and a detector which detects an intensity distribution of reflected light reflected by the electro-optic device, wherein the electro-optic device includes an electro-optic crystal layer;

a transparent conductive layer located at a light-incidence side of the electro-optic crystal layer; and a reflection preventing layer located between the electro-optic crystal layer and the transparent conductive layer.

10. A circuit pattern detecting apparatus comprising:

an electro-optic device located near a circuit board on which a circuit pattern is formed, and having a polarization plane that changes in accordance with an index of birefringence varying with an electric field;

a voltage application circuit which applies a voltage between the circuit pattern and the electro-optic device in order to apply the electro-optic device with an electric field determined in accordance with the circuit pattern;

a light source which irradiates the electro-optic device with light; and a detector which detects an intensity distribution of reflected light reflected by the electro-optic device in synchronism with application of the voltage, wherein the electro-optic device includes an electro-optic crystal layer;

a transparent conductive layer located at a light-incidence side of the electro-optic crystal layer; and a reflection preventing layer located between the electro-optic crystal layer and the transparent conductive layer.

11. A circuit pattern detecting apparatus comprising:

an electro-optic device located near a circuit board on which a circuit pattern is formed, and having a polarization plane that changes in accordance with an index of birefringence varying with an electric field;

a voltage application circuit which applies a voltage between the circuit pattern and the electro-optic device in order to apply the electric device with an electric field determined in accordance with the circuit pattern;

a light source which irradiates the electro-optic device with light;

a detector which detects an intensity distribution of reflected light reflected by the electro-optic device; and a control device which controls the light irradiation from the light source or the light incidence to the detector such that irradiation light or incidence light is changed into pulse light, wherein the electro-optic device includes an electro-optic crystal layer;

a transparent conductive layer located at a light-incidence side of the electro-optic crystal layer; and a reflection preventing layer located between the electro-optic crystal layer and the transparent conductive layer.

* * * * *

UNITED STATES PATENT AND TRADEMARK OFFICE
CERTIFICATE OF CORRECTION

PATENT NO. : 6,894,514 B2 Page 1 of 1
APPLICATION NO. : 10/295847
DATED : May 17, 2005
INVENTOR(S) : Takayuki Yanagisawa It is certified that error appears in the above-identified patent and that said Letters Patent is hereby corrected as shown below:

Column 20, Line 16, (claim 5, line 5), change "end" to --and--.

Signed and Sealed this

Twenty-first Day of November, 2006

JON W. DUDAS
*Director of the United States Patent and Trademark Office*